United States Patent
Barberio et al.

(10) Patent No.: US 11,964,026 B2
(45) Date of Patent: *Apr. 23, 2024

(54) LAYER-BY-LAYER NANOPARTICLES FOR CYTOKINE THERAPY IN CANCER TREATMENT

(71) Applicant: Massachusetts Institute of Technology, Cambridge, MA (US)

(72) Inventors: Antonio Eric Barberio, Cambridge, MA (US); Santiago Correa Echavarria, Allston, MA (US); Mariane Bandeira Melo, Stoneham, MA (US); Talar Tokatlian, Cambridge, MA (US); Erik Christopher Dreaden, Atlanta, GA (US); Paula T. Hammond, Newton, MA (US); Darrell J. Irvine, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/892,496

(22) Filed: Aug. 22, 2022

(65) Prior Publication Data
US 2023/0201367 A1 Jun. 29, 2023

Related U.S. Application Data

(63) Continuation of application No. 16/175,311, filed on Oct. 30, 2018, now Pat. No. 11,419,947.

(60) Provisional application No. 62/578,730, filed on Oct. 30, 2017.

(51) Int. Cl.
| | | |
|---|---|---|
| *A61K 47/54* | (2017.01) | |
| *A61K 9/00* | (2006.01) | |
| *A61K 9/127* | (2006.01) | |
| *A61K 38/20* | (2006.01) | |
| *A61K 47/69* | (2017.01) | |
| *A61P 35/00* | (2006.01) | |

(52) U.S. Cl.
CPC ........ *A61K 47/6911* (2017.08); *A61K 9/0019* (2013.01); *A61K 9/1271* (2013.01); *A61K 38/208* (2013.01); *A61K 47/544* (2017.08); *A61P 35/00* (2018.01)

(58) Field of Classification Search
None
See application file for complete search history.

(56) References Cited

U.S. PATENT DOCUMENTS

| | | |
|---|---|---|
| 3,266,987 A | 8/1966 | Crowley et al. |
| 3,710,795 A | 1/1973 | Higuchi et al. |
| 3,962,414 A | 6/1976 | Michaels |
| 4,191,811 A | 3/1980 | Hodgdon |
| 4,250,029 A | 2/1981 | Kiser et al. |
| 4,460,563 A | 7/1984 | Calanchi |
| 4,638,045 A | 1/1987 | Kohn et al. |
| 4,794,000 A | 12/1988 | Ecanow |
| 4,806,355 A | 2/1989 | Goosen et al. |
| 4,806,621 A | 2/1989 | Kohn et al. |
| 4,946,929 A | 8/1990 | D'Amore et al. |
| 5,010,167 A | 4/1991 | Ron et al. |
| 5,015,476 A | 5/1991 | Cochrum et al. |
| 5,019,379 A | 5/1991 | Domb et al. |
| 5,093,489 A | 3/1992 | Diamantoglou |
| 5,114,719 A | 5/1992 | Sabel et al. |
| 5,208,111 A | 5/1993 | Decher et al. |
| 5,245,012 A | 9/1993 | Lombari et al. |
| 5,263,992 A | 11/1993 | Guire |
| 5,270,419 A | 12/1993 | Domb |
| 5,364,634 A | 11/1994 | Lew |
| 5,397,848 A | 3/1995 | Yang et al. |
| 5,399,665 A | 3/1995 | Barrera et al. |
| 5,462,990 A | 10/1995 | Hubbell et al. |
| 5,512,131 A | 4/1996 | Kumar et al. |
| 5,512,600 A | 4/1996 | Mikos et al. |
| 5,514,378 A | 5/1996 | Mikos et al. |
| 5,518,767 A | 5/1996 | Rubner et al. |
| 5,536,573 A | 7/1996 | Rubner et al. |
| 5,539,083 A | 7/1996 | Cook et al. |
| 5,576,881 A | 11/1996 | Doerr et al. |
| 5,630,941 A | 5/1997 | Burger et al. |
| 5,660,873 A | 8/1997 | Nikolaychik et al. |
| 5,696,175 A | 12/1997 | Mikos et al. |
| 5,700,559 A | 12/1997 | Sheu et al. |
| 5,714,166 A | 2/1998 | Tomalia et al. |
| 5,716,303 A | 2/1998 | Scatterday |
| 5,716,404 A | 2/1998 | Vacanti et al. |

(Continued)

FOREIGN PATENT DOCUMENTS

| | | |
|---|---|---|
| CN | 1679518 A | 10/2005 |
| DE | 19812083 A1 | 9/1999 |

(Continued)

OTHER PUBLICATIONS

Chikh et al (Biochimica et Biophysica Acta, 1567, 2002, 204-212) (Year: 2002).*
Lieschke et al (Nature Biotechnology, 15, 1997, 35-40) (Year: 1997).*
Pan et al (Molecular Therapy, 20(5), 927-937, 2012) (Year: 2012).*
Office Action for U.S. Appl. No. 12/542,267, entitled "Controlled Delivery of Bioactive Agents from Decompostable Films", dated Mar. 27, 2014.
Office Action for U.S. Appl. No. 13/115,107, entitled "Multilayer Coating Compositions, Coated Substrates and Methods Thereof", dated Jan. 28, 2015.

(Continued)

*Primary Examiner* — Celeste A Roney
(74) *Attorney, Agent, or Firm* — Foley Hoag LLP; Alexander Akhiezer; Lawrence P. Tardibono

(57) ABSTRACT

Disclosed are particles for delivering cytokinese, such as IL-12, for the treatment of cancer. The particles comprise cytokines non-covalently bound to liposomes, where the liposomes are coated with polyelectrolytes.

21 Claims, 22 Drawing Sheets

(56) References Cited

U.S. PATENT DOCUMENTS

| Patent/Pub. No. | Date | Inventor(s) |
|---|---|---|
| 5,716,709 A | 2/1998 | Ferguson et al. |
| 5,736,372 A | 4/1998 | Vacanti et al. |
| 5,770,417 A | 6/1998 | Vacanti et al. |
| 5,797,898 A | 8/1998 | Santini, Jr. et al. |
| 5,804,178 A | 9/1998 | Vacanti et al. |
| 5,807,636 A | 9/1998 | Sheu et al. |
| 5,837,377 A | 11/1998 | Sheu et al. |
| 5,837,752 A | 11/1998 | Shastri et al. |
| 5,858,746 A | 1/1999 | Hubbell et al. |
| 5,902,599 A | 5/1999 | Anseth et al. |
| 5,902,800 A | 5/1999 | Green et al. |
| 5,904,927 A | 5/1999 | Amiji |
| 5,962,520 A | 10/1999 | Smith et al. |
| 6,022,590 A | 2/2000 | Ferguson et al. |
| 6,060,582 A | 5/2000 | Hubbell et al. |
| 6,089,853 A | 7/2000 | Biebuyck et al. |
| 6,095,148 A | 8/2000 | Shastri et al. |
| 6,103,266 A | 8/2000 | Tapolsky et al. |
| 6,114,099 A | 9/2000 | Liu et al. |
| 6,123,681 A | 9/2000 | Brown |
| 6,123,727 A | 9/2000 | Vacanti et al. |
| 6,127,143 A | 10/2000 | Gunasekaran |
| 6,131,211 A | 10/2000 | Hennessey |
| 6,180,239 B1 | 1/2001 | Whitesides et al. |
| 6,180,329 B1 | 1/2001 | Paris |
| 6,235,224 B1 | 5/2001 | Mathiowitz et al. |
| 6,235,334 B1 | 5/2001 | Donovan |
| 6,245,537 B1 | 6/2001 | Williams et al. |
| 6,267,776 B1 | 7/2001 | O'Connell |
| 6,267,784 B1 | 7/2001 | Benz et al. |
| 6,302,848 B1 | 10/2001 | Larson et al. |
| 6,310,188 B1 | 10/2001 | Mukherjee |
| 6,312,727 B1 | 11/2001 | Schacht et al. |
| 6,325,810 B1 | 12/2001 | Hamilton et al. |
| 6,337,198 B1 | 1/2002 | Levene et al. |
| 6,372,244 B1 | 4/2002 | Antanavich et al. |
| 6,379,690 B2 | 4/2002 | Blanchard et al. |
| 6,395,734 B1 | 5/2002 | Tang et al. |
| 6,402,918 B1 | 6/2002 | Schlenoff et al. |
| 6,433,134 B1 | 8/2002 | Patron et al. |
| 6,447,887 B1 | 9/2002 | Claus et al. |
| 6,451,871 B1 | 9/2002 | Winterton et al. |
| 6,479,146 B1 | 11/2002 | Caruso et al. |
| 6,492,096 B1 | 12/2002 | Liu et al. |
| 6,497,729 B1 | 12/2002 | Moussy et al. |
| 6,699,501 B1 | 3/2004 | Neu et al. |
| 6,716,813 B2 | 4/2004 | Lim et al. |
| 6,740,643 B2 | 5/2004 | Wolff et al. |
| 6,743,521 B2 | 6/2004 | Hubbell et al. |
| 6,833,192 B1 | 12/2004 | Caruso et al. |
| 6,860,980 B2 | 3/2005 | Locascio et al. |
| 6,896,926 B2 | 5/2005 | Qiu et al. |
| 6,919,373 B1 | 7/2005 | Lam et al. |
| 6,998,115 B2 | 2/2006 | Langer et al. |
| 7,045,087 B2 | 5/2006 | Kotov |
| 7,045,146 B2 | 5/2006 | Caruso et al. |
| 7,101,575 B2 | 9/2006 | Donath et al. |
| 7,101,947 B2 | 9/2006 | Schlenoff et al. |
| 7,112,361 B2 | 9/2006 | Lynn et al. |
| 7,223,327 B2 | 5/2007 | Schlenoff et al. |
| 7,303,814 B2 | 12/2007 | Lamberti et al. |
| 7,348,399 B2 | 3/2008 | Haynie |
| 7,364,585 B2 | 4/2008 | Weber |
| 7,365,142 B2 | 4/2008 | Schlenoff et al. |
| 7,427,354 B2 | 9/2008 | Eto |
| 7,427,394 B2 | 9/2008 | Anderson et al. |
| 7,491,263 B2 | 2/2009 | Wang et al. |
| 7,879,575 B2 | 2/2011 | Kricka et al. |
| 8,105,652 B2 | 1/2012 | Wood et al. |
| 8,685,538 B2 * | 4/2014 | Torchilin ............ A61K 9/5169 428/407 |
| 9,198,875 B2 | 12/2015 | Smith et al. |
| 9,320,750 B2 | 4/2016 | Yaffe et al. |
| 9,393,217 B2 | 7/2016 | Hammond et al. |
| 9,463,244 B2 | 10/2016 | Castleberry et al. |
| 9,610,252 B2 | 4/2017 | DeMuth et al. |
| 9,737,557 B2 | 8/2017 | Hammond et al. |
| 10,278,927 B2 | 5/2019 | Hammond et al. |
| 11,419,947 B2 | 8/2022 | Barberio et al. |
| 2002/0053514 A1 | 5/2002 | Locascio et al. |
| 2002/0131933 A1 | 9/2002 | Delmotte |
| 2002/0131951 A1 | 9/2002 | Langer et al. |
| 2002/0187197 A1 | 12/2002 | Caruso et al. |
| 2003/0059398 A1 | 3/2003 | Ranger et al. |
| 2003/0113368 A1 | 6/2003 | Nomoto et al. |
| 2003/0124368 A1 | 7/2003 | Lynn et al. |
| 2003/0236573 A1 | 12/2003 | Evans et al. |
| 2004/0013721 A1 | 1/2004 | Antipov et al. |
| 2004/0020423 A1 | 2/2004 | Lewis et al. |
| 2004/0044100 A1 | 3/2004 | Schlenoff et al. |
| 2004/0052865 A1 | 3/2004 | Gower et al. |
| 2004/0149572 A1 | 8/2004 | Schlenoff et al. |
| 2004/0258753 A1 | 12/2004 | Demeester et al. |
| 2005/0019404 A1 | 1/2005 | Sung et al. |
| 2005/0089890 A1 | 4/2005 | Cubicciotti |
| 2005/0152955 A1 | 7/2005 | Akhave et al. |
| 2005/0208100 A1 | 9/2005 | Weber et al. |
| 2005/0265961 A1 | 12/2005 | Langer et al. |
| 2005/0276841 A1 | 12/2005 | Davis et al. |
| 2006/0118754 A1 | 6/2006 | Lapen |
| 2006/0127437 A1 | 6/2006 | Kennedy et al. |
| 2006/0198897 A1 | 9/2006 | Pacetti et al. |
| 2006/0216494 A1 | 9/2006 | Furedi-Milhofer et al. |
| 2006/0246112 A1 | 11/2006 | Snyder et al. |
| 2006/0260777 A1 | 11/2006 | Rashba-Step et al. |
| 2007/0020469 A1 | 1/2007 | Wood et al. |
| 2007/0077276 A1 | 4/2007 | Haynie |
| 2007/0083186 A1 | 4/2007 | Carter et al. |
| 2007/0129792 A1 | 6/2007 | Picart et al. |
| 2007/0141100 A1 | 6/2007 | Sung et al. |
| 2007/0197568 A1 | 8/2007 | Bunn et al. |
| 2007/0276330 A1 | 11/2007 | Beck et al. |
| 2008/0139450 A1 | 6/2008 | Madhyastha et al. |
| 2008/0200982 A1 | 8/2008 | Your |
| 2008/0213461 A1 | 9/2008 | Gill et al. |
| 2008/0228280 A1 | 9/2008 | Cohen et al. |
| 2008/0248108 A1 | 10/2008 | Krotz et al. |
| 2008/0286345 A1 | 11/2008 | Lynn et al. |
| 2008/0311177 A1 | 12/2008 | Hammond et al. |
| 2009/0018029 A1 | 1/2009 | Miao et al. |
| 2009/0047517 A1 | 2/2009 | Caruso et al. |
| 2009/0053139 A1 | 2/2009 | Shi et al. |
| 2009/0061006 A1 | 3/2009 | Leuschner et al. |
| 2009/0061451 A1 | 3/2009 | Achim et al. |
| 2009/0088479 A1 | 4/2009 | Allmendinger et al. |
| 2009/0088679 A1 | 4/2009 | Wood et al. |
| 2009/0155326 A1 | 6/2009 | Mack et al. |
| 2009/0170179 A1 | 7/2009 | Lynn et al. |
| 2009/0214615 A1 | 8/2009 | Zhao |
| 2009/0246142 A1 | 10/2009 | Bhatia et al. |
| 2009/0258045 A1 | 10/2009 | Chuang et al. |
| 2009/0263468 A1 | 10/2009 | McAnulty et al. |
| 2009/0275906 A1 | 11/2009 | Berland et al. |
| 2010/0003499 A1 | 1/2010 | Krogman et al. |
| 2010/0016439 A1 | 1/2010 | Thomes et al. |
| 2010/0040674 A1 | 2/2010 | Smith et al. |
| 2010/0143677 A1 | 6/2010 | Lee et al. |
| 2010/0189683 A1 | 7/2010 | Holmlund et al. |
| 2011/0038939 A1 | 2/2011 | Lvov et al. |
| 2011/0114244 A1 | 5/2011 | Yoo et al. |
| 2011/0143127 A1 | 6/2011 | Gupta et al. |
| 2011/0189292 A1 | 8/2011 | Lebreton et al. |
| 2011/0244048 A1 | 10/2011 | Amiji et al. |
| 2011/0301209 A1 | 12/2011 | Zaknoen et al. |
| 2012/0015146 A1 | 1/2012 | Advincula et al. |
| 2012/0027837 A1 | 2/2012 | DeMuth et al. |
| 2012/0058355 A1 | 3/2012 | Lee et al. |
| 2012/0156389 A1 | 6/2012 | Kotov |
| 2012/0207795 A1 | 8/2012 | Zink et al. |
| 2012/0277719 A1 | 11/2012 | Shukla et al. |
| 2012/0277852 A1 | 11/2012 | Shukla et al. |
| 2013/0190890 A1 | 7/2013 | Shah et al. |
| 2013/0243693 A1 | 9/2013 | Omenetto et al. |
| 2013/0273137 A1 | 10/2013 | Mandell et al. |

(56) References Cited

U.S. PATENT DOCUMENTS

| | | |
|---|---|---|
| 2014/0011759 A1 | 1/2014 | Yaffe et al. |
| 2014/0039575 A1 | 2/2014 | Bradley |
| 2014/0093575 A1* | 4/2014 | Hammond ......... A61K 31/4188 424/490 |
| 2014/0302116 A1 | 10/2014 | Castleberry et al. |
| 2014/0328931 A1 | 11/2014 | Hammond et al. |
| 2015/0086599 A1 | 3/2015 | Hammond et al. |
| 2015/0125879 A1 | 5/2015 | Li et al. |
| 2015/0202304 A1 | 7/2015 | Kaplan et al. |
| 2015/0290669 A1 | 10/2015 | Li et al. |
| 2016/0038632 A1 | 2/2016 | Shah et al. |
| 2017/0181981 A1 | 6/2017 | Hammond et al. |
| 2017/0258738 A1 | 9/2017 | DeMuth et al. |
| 2020/0000713 A1 | 1/2020 | Bennett et al. |
| 2020/0377929 A1 | 12/2020 | Irvine et al. |
| 2023/0242969 A1 | 8/2023 | Irvine et al. |

FOREIGN PATENT DOCUMENTS

| | | |
|---|---|---|
| DE | 29907804 U1 | 10/1999 |
| EP | 0 443 809 A2 | 8/1991 |
| EP | 1 116 516 A1 | 7/2001 |
| EP | 2 162 283 A2 | 3/2010 |
| EP | 2 566 468 A2 | 3/2013 |
| EP | 2 701 908 A1 | 3/2014 |
| GB | 1213803 A | 11/1970 |
| GB | 1213805 A | 11/1970 |
| WO | WO-1995/11748 A1 | 5/1995 |
| WO | WO-1995/34595 A1 | 12/1995 |
| WO | WO-1996/03147 A1 | 2/1996 |
| WO | WO-97/08315 A1 | 3/1997 |
| WO | WO-1998/03573 A1 | 1/1998 |
| WO | WO-98/17330 A1 | 4/1998 |
| WO | WO-1998/47948 A1 | 10/1998 |
| WO | WO-1999/47253 A1 | 9/1999 |
| WO | WO-99/59647 A1 | 11/1999 |
| WO | WO-1999/56878 A1 | 11/1999 |
| WO | WO-2000/77281 A1 | 12/2000 |
| WO | WO-2001/57118 A2 | 8/2001 |
| WO | WO-2001/94441 A1 | 12/2001 |
| WO | WO-2002/12888 A2 | 2/2002 |
| WO | WO-2002/085500 A1 | 10/2002 |
| WO | WO-2003/035716 A1 | 5/2003 |
| WO | WO-2004/032974 A1 | 4/2004 |
| WO | WO-2006/051227 A1 | 5/2006 |
| WO | WO-2006/079928 A2 | 8/2006 |
| WO | WO-2006/086391 A2 | 8/2006 |
| WO | WO-2007/003054 A1 | 1/2007 |
| WO | WO-2007/140391 A2 | 12/2007 |
| WO | WO-2007/140402 A1 | 12/2007 |
| WO | WO-2008/057127 A2 | 5/2008 |
| WO | WO-2008/118133 A2 | 10/2008 |
| WO | WO-2008/157372 A2 | 12/2008 |
| WO | WO-2009/051734 A1 | 4/2009 |
| WO | WO-2009/117473 A2 | 9/2009 |
| WO | WO-2010/021973 A2 | 2/2010 |
| WO | WO-2010/026450 A1 | 3/2010 |
| WO | WO-2010/059963 A2 | 5/2010 |
| WO | WO-2010/097814 A2 | 9/2010 |
| WO | WO-2010/120531 A2 | 10/2010 |
| WO | WO-2011/140136 A2 | 11/2011 |
| WO | WO-2012/149492 A1 | 11/2012 |
| WO | WO-2012/149494 A2 | 11/2012 |
| WO | WO-2013/110047 A1 | 7/2013 |
| WO | WO-2013/163234 A1 | 10/2013 |
| WO | WO-2013/169479 A1 | 11/2013 |
| WO | WO-2014/012099 A1 | 1/2014 |
| WO | WO-2014/059269 A2 | 4/2014 |
| WO | WO-2014/066862 A1 | 5/2014 |
| WO | WO-2014/093934 A1 | 6/2014 |
| WO | WO-2014/134029 A1 | 9/2014 |
| WO | WO-2014/150074 A1 | 9/2014 |
| WO | WO-2015/048315 A1 | 4/2015 |
| WO | WO-2016/022131 A1 | 2/2016 |
| WO | WO-2017/031060 A1 | 2/2017 |
| WO | WO-2017/065696 A2 | 4/2017 |
| WO | WO-2017/117188 A1 | 7/2017 |
| WO | WO-2018/136754 A1 | 7/2018 |
| WO | WO-2018/202922 A1 | 11/2018 |
| WO | WO-2019/089567 A1 | 5/2019 |
| WO | WO-2021/002984 A1 | 1/2021 |

OTHER PUBLICATIONS

Office Action for U.S. Appl. No. 10/280,268, entitled: Methods Of Making Decomposable Thin Films Of Polyelectrolytes And Uses Thereof, dated Jul. 6, 2005.

Office Action for U.S. Appl. No. 10/280,268, entitled: Methods Of Making Decomposable Thin Films Of Polyelectrolytes And Uses Thereof, dated Jun. 29, 2006.

Office Action for U.S. Appl. No. 10/280,268, entitled: Methods Of Making Decomposable Thin Films Of Polyelectrolytes And Uses Thereof, dated Nov. 2, 2004.

Office Action for U.S. Appl. No. 11/459,979, entitled: Methods Of Making Decomposable Thin Films Of Polyelectrolytes And Uses Thereof, dated Jul. 23, 2010.

Office Action for U.S. Appl. No. 11/459,979, entitled: Methods Of Making Decomposable Thin Films Of Polyelectrolytes And Uses Thereof, dated Oct. 29, 2009.

Office Action for U.S. Appl. No. 11/815,718, entitled: "Electrochemically Degradable Layer-By-Layer Thin Films", dated Mar. 26, 2012.

Office Action for U.S. Appl. No. 11/815,718, entitled: "Electrochemically Degradable Layer-By-Layer Thin Films", dated Mar. 27, 2014.

Office Action for U.S. Appl. No. 11/815,718, entitled: "Electrochemically Degradable Layer-By-Layer Thin Films", dated Nov. 27, 2012.

Office Action for U.S. Appl. No. 12/139,151, entitled: "Self Assembled Films For Protein And Drug Delivery Applications", dated Jun. 11, 2014.

Office Action for U.S. Appl. No. 12/139,151, entitled: "Self Assembled Films For Protein And Drug Delivery Applications", dated Jun. 20, 2012.

Office Action for U.S. Appl. No. 12/139,151, entitled: "Self Assembled Films For Protein And Drug Delivery Applications", dated Sep. 22, 2011.

Office Action for U.S. Appl. No. 12/542,267, entitled: "Controlled Delivery Of Bioactive Agents From Decomposable Films", dated Aug. 17, 2012.

Office Action for U.S. Appl. No. 12/542,267, entitled: "Controlled Delivery Of Bioactive Agents From Decomposable Films", dated Jun. 7, 2013.

Office Action for U.S. Appl. No. 12/542,267, entitled: "Controlled Delivery Of Bioactive Agents From Decomposable Films", dated Mar. 31, 2014.

Final Office Action for U.S. Appl. No. 12/542,267, entitled: "Controlled Delivery of Bioactive Agents From Decomposable Film," dated Mar. 11, 2015.

Office Action for U.S. Appl. No. 13/869,012, "Compositions and Methods of Treatment of Drug Resistant Cancers," dated Apr. 7, 2015.

Office Action for U.S. Appl. No. 13/115,107, entitled: "Multilayer Coating Compositions, Coated Substrates and Methods Thereof", dated Apr. 17, 2014.

Office Action for U.S. Appl. No. 13/459,066, entitled: "Coating Compositions, Methods and Coated Devices", dated Oct. 15, 2014.

Office Action for U.S. Appl. No. 13/459,069 entitled: "Coating Compositions, Methods And Coated Devices", dated Oct. 23, 2014.

Office Action for U.S. Appl. No. 13/695,836 entitled: "Drug Delivery Coating And Devices", dated Nov. 28, 2014.

Office Action for U.S. Appl. No. 13/746,902 entitled: "Compositions and Methods for Coating," dated Jan. 2, 2015.

Office Action for U.S. Appl. No. 13/869,015 entitled: "Stable Layer-By-Layer Coated Particles", dated Nov. 21, 2014.

Office Action for U.S. Appl. No. 14/190,983, "Nucleic Acid Particles, Methods; And Use Thereof", dated Jan. 29, 2015.

(56) References Cited

OTHER PUBLICATIONS

Abeloff et al., "Chapter 95: Cancer of the Breast," Abeloff's Clinical Oncology, Fourth Edition, Churchill Livingstone Elsevier, pp. 1875-1943 (2008).
Abramoff et al., "Image Processing with ImageJ," Biophotonics International, 11: 36-42 (2004).
Absolom et al., "Protein adsorption to polymer particles: role of surface properties," J Biomed Mater Res, 21(2): 161-71 (1987).
Afonin et al., "In vitro assembly of cubic RNA-based scaffolds designed in silico," Nature Nanotechnol, 5: 676-682 (2010).
Ai et al., "Biomedical applications of electrostatic layer-by-layer nano-assembly of polymers, enzymes, and nanoparticles," Cell Biochem Biophys, 39(1):23-43 (2003).
Akinc et al., "A combinatorial library of lipid-like materials for delivery of RNAi therapeutics," Nature Biotechnol, 26:561-569 (2008).
Akinc et al., "Synthesis of poly(β-amino ester)s optimized for highly effective gene delivery," Bioconjugate Chem, 14:979-988 (2003).
Albeck et al., "Modeling a Snap-Action, Variable-Delay Switch Controlling Extrinsic Cell Death," PLoS Biology, 6(12): 2831-2852 (2008).
Albrektsson et al., "Osteoinduction, osteoconduction and osseointegration," Eur Spine J, 10(2):S96-101(2001).
Alsberg et al., "Craniofacial tissue engineering," Crit Rev Oral Biol Med, 12(1):64-75 (2001).
Alsberg et al., "Regulating bone formation via controlled scaffold degradation," J Dent Res, 82(11): 903-908 (2003).
Alvarez-Roman et al., "Skin penetration and distribution of polymeric nanoparticles," J Controlled Release, 99:53-62 (2004).
Alves et al., "Self assembling and crosslinking of polyelectrolyte multilayer films of chitosan and alginate studied by QCM and IR spectroscopy," Macromol Biosci, 9(8):776-85 (2009).
Ambros, "The functions of animal microRNAs," Nature, 431:350-355 (2004).
Anderson et al., "Biodegradation and Biocompatibility of PLA and PLGA Microspheres," Adv Drug Delivery Rev, 28: 5-24 (1997).
Anderson et al., "Semi-Automated Synthesis and Screening of a Large Library of Degradable Cationic Polymers for Gene Delivery," Angew Chem Int Ed, 42: 3151-3158 (2003).
Anderson, "Human Gene Therapy," Nature, 392: 25-30 (1998).
Ando et al., "PLGA Microspheres Containing Plasmid DNA: Preservation of Supercoiled DNA via Cryopreparation and Carbohydrate Stabilization," J Pharm Sci, 88: 126-130 (1999).
Antipov et al., "Sustained Release Properties of Polyelectrolyte Multilayer Capsules," J Phys Chem B, 105: 2281-2284 (2001).
Ariga et al., "Layer-by-layer assembly as a versatile bottom-up nanofabrication technique for exploratory research and realistic application," Phys Chem Chem Phys, 9(19):2319-40 (2007).
Armitage et al., "Hairpin-Forming Peptide Nucleic Acid Oligomers," Biochemistry, 37(26):9417-9425 (1998).
Bakhtiar, "Peptide nucleic acids: deoxyribonucleic acid mimics with a peptide backbone," Biochemical Education, 26:277-280 (1998).
Balabushevich et al., "Protein-loaded microspheres prepared by sequential adsorption of dextran sulphate and protamine on melamine formaldehyde core," J Microencapsul, 26(7):571-9 (2009).
Balko et al., "Gene Expression Patterns that Predict Sensitivity to Epidermal Growth Factor Receptor Tyrosine Kinase Inhibitors in Lung Cancer Cell Lines and Human Lung Tumors," BMC Genomics, 7: 289-302 (2006).
Barberio, "Layer-by-Layer Nanoparticles for Cytokine Therapy," 2018 ACS Annual Meeting Boston (oral), 1-23 (Aug. 22, 2018).
Barberio, "Layer-by-Layer Nanoparticles for Cytokine Therapy," AIChE Bioengineering and Translational Medicine, presentation slides 1-20 (Sep. 27, 2018).
Barker et al., "Fabrication, Derivatization and Applications of Plastic Microfluidic Devices," Proceedings of SPIE—The International Society for Optical Engineering, 112-118 (2001).

Barrera et al., "Synthesis and RGD Peptide Modification of a New Biodegradable Copolymer: Poly (lactic acid-co-lysine)," J Am Chem Soc, 115: 11010-11011 (1993).
Bartel, "MicroRNAs: Genomics, Review Biogenesis, Mechanism, and Function," Cell, 116:281-297 (2004).
Baselga et al., "Phase II Multicenter Study of the Antiepidermal Growth Factor Receptor Monoclonal Antibody Cetuximab in Combination with Platinum-Based Chemotherapy in Patients with Platinum-Refractory Metastatic and/or Recurrent Squamous Cell Carcinoma of the Head and Neck," J. of Clinical Oncology, 23(24): 5568-5577 (2005).
Bass, "RNA Interference the Short Answer," Nature, 411: 428-429 (2001).
Behr, "Synthetic Gene-Transfer Vectors," Acc Chem Res, 26: 274-278 (1993).
Behr, "The Proton Sponge: A Trick to Enter Cells the Viruses Did Not Exploit," Chimia, 51: 34-36 (1997).
Benkirane-Jessel et al., "Build-up of Polypeptide Multilayer Coatings with Anti-Inflammatory Properties Based on the Embedding of Piroxicam-Cyclodextrin Complexes," Advanced Functional Materials, 14(2): 174-182 (2004).
Berg et al., "Controlling mammalian cell interactions on patterned polyelectrolyte multilayer surfaces," Langmuir, 20(4): 1362-8 (2004).
Bernards et al., "Nanotemplating of Biodegradable Polymer Membranes for Constant-Rate Drug Delivery," Adv Mater, 22: 2358-2362 (2010).
Bershteyn et al., "Polymer-supported lipid shells, onions, and flowers," Soft Matter, 4(9):1787-1791 (2008).
Beyer et al., "Periodic DNA nanotemplates synthesized by rolling circle amplification," Nano Lett, 5: 719-722 (2005).
Biggs et al., "The use of nanoscale topography to modulate the dynamics of adhesion formation in primary osteoblasts and ERK/MAPK signalling in STRO-1+ enriched skeletal stem cells," Biomaterials, 30(28):5094-103 (2009).
Bins et al., "A rapid and potent DNA vaccination strategy defined by in vivo monitoring of antigen expression," Nat. Med, 11:899-904 (2005).
Blacklock et al., "Cross-linked bioreducible layer-by-layer films for increased cell adhesion and transgene expression" J Phys Chem B, 114(16):5283-91 (2010).
Boes et al., "T-cell engagement of dendritic cells rapidly rearranges MHC class II transport," Nature, 418: 983-988 (2002).
Bonewald et al., "Von Kossa staining alone is not sufficient to confirm that mineralization in vitro represents bone formation," Calcified Tissue Int, 72(5):537-47 (2003).
Bott, "Applications of "Wired" Enzyme Electrodes," Current Separations, 21(1): 3-6 (2004).
Boudou et al., "Internal composition versus the mechanical properties of polyelectrolyte multilayer films: the influence of chemical cross-linking," Langmuir, 25(24):13809-19 (2009).
Boudou et al., "Multiple functionalities of polyelectrolyte multilayer films: new biomedical applications," Adv Mater, 22(4):441-467 (2010).
Boussif et al., "A Versatile Vector for Gene and Oligonucleotide Transfer into Cells in Culture and In Vivo: Polyethylenimine," Proc Natl Acad Sci, USA, 92: 7297-7301 (1995).
Brama et al., "Effect of titanium carbide coating on the osseointegration response in vitro and in vivo," Biomaterials, 28(4):595-608 (2007).
Brange et al., "Insulin formulation and delivery," Pharm Biotechnol, 10:343-409 (1997).
Brazeau et al., "In Vitro Myotoxicity of Selected Cationic Macromolecules Used in Non-Viral Gene Delivery," Pharm Res, 15: 680-684 (1998).
Breger et al., "Synthesis of "click" alginate hydrogel capsules and comparison of their stability, water swelling, and diffusion properties with that of $Ca^{+2}$ crosslinked alginate capsules," J. Biomed. Mat. Res. B Appl. Biomat., 103:1120-1132 (2015).
Brewer et al., "Condensation of DNA by spermatid basic nuclear proteins," J Biol Chem, 277(41):38895-900 (2002).
Brewster et al., "Cyclodextrins as Pharmaceutical Solubilizers," Advanced Drug Delivery Reviews, 59: 645-666 (2007).

(56) References Cited

OTHER PUBLICATIONS

Brock et al., "Liquid biopsy for cancer screening, patient stratification and monitoring," Transl Cancer Res, 4(3):280-290 (2015).
Bryzgunova et al., "Isolation and Comparative Study of Cell?Free Nucleic Acids from Human Urine," Annals of the New York Academy of Sciences, 1075:334-340 (2006).
Burke et al., "pH Responsive Properties of Multilayered Poly(L-lysine)/Hyaluronic Acid Surfaces," Biomacromolecules, 4: 1773-1783 (2003).
Buser et al., "The Crystal Structure of Prussian Blue: Fe4[Fe(CN)5]3XH20," Inorganic Chemistry, 16(11): 2704-2710 (1977).
Calvo et al., "Donnan Permselectivity in Layer-by-Layer Self-Assembled Redox Polyelectrolyte Thin Film," J Am Chem Soc, 124: 8490-8497 (2002).
Carey et al., "EGFR Inhibition with Cetuximab Added to Carboplatin in Metastatic Triple-negative (basal-like) Breast Cancer," Supplement to Journal of Clinical Oncology, ASCO Annual Meeting Proceedings, TBCRC 001: Clinical Science Symposium, 43S (2009).
Carpenter et al., "A Single-Film Electrochromic Device," J Electrochem Soc, 137(8): 2464-2467 (1990).
Carpenter et al., "CellProfiler: Image Analysis Software for Identifying and Quantifying Cell Phenotypes," Genome Biology, 7(10): R100-R100.11 (2006).
Carragee et al., "A critical review of recombinant human bone morphogenetic protein-2 trials in spinal surgery: emerging safety concerns and lessons learned," Spine J, 11(6): 471-491 (2011).
Carrell et al., "The aetiology of sperm protamine abnormalities and their potential impact on the sperm epigenome," Int J Androl, 31(6):537-45 (2008).
Caruso, "COLL 34-Polymer Design And Assembly For Next-Generation Particle Delivery," Abstracts of Papers, The 237th ACS National Meeting and Exposition, Salt Lake City, UT (Mar. 22-26, 2009).
Castleberry et al., "220-Surface Mediated Delivery of siRNA from Layer-By-Layer Assembled Polyelectrolyte Films for the Acceleration of Wound Healing," Abstracts of Papers, 244th ACS National Meeting and Exposition, Philadelphia, PA (Aug. 19-23, 2012).
Castleberry et al., "Nanolayered siRNA Dressing for Sustained Localized Knockdown," ACS Nano, 7(6): 5251-5261 (2013).
Cavalieri et al., "Assembly and functionalization of DNA-polymer microcapsules," ACS Nano 3(1):234-240 (2009).
Chan et al., "Cell-free nucleic acids in plasma, serum and urine: a new tool in molecular diagnosis," Ann. Clin. Biochem., 40:122-130 (2003).
Chen et al., "Characterization of microRNAs in serum: a novel class of biomarkers for diagnosis of cancer and other diseases," Cell Res., 18:997-1006 (2008).
Chen, "Preparation, Characterization, and Electrocatalytic Oxidation Properties of Iron, Cobalt, Nickel, and Indium Hexacyanoferrate," Journal of Electroanalytical Chemistry, 521: 29-52 (2002).
Chikh et al., "Attaching histidine-tagged peptides and proteins to lipid-based carriers through use of metal-ion-chelating lipids," Biochim Biophys Acta 1567:204-212 (2002).
Cho, "MicroRNAs: Potential biomarkers for cancer diagnosis, prognosis and targets for therapy," The International Journal of Biochemistry & Cell Biology, 42(8):1273-1281 (2010).
Choksakulnimitr et al., "In Vitro Cytotoxicity of Macromolecules in Different Cell Culture Systems," Journal of Controlled Release 34: 233-241 (1995).
Chou et al., "Quantitative Analysis of Dose-Effect Relationships: The Combined Effects of Multiple Drugs or Enzymes Inhibitors," Advances in Enzyme Regulation, 22: 27-55 (1984).
Christensen et al., "Heparin Coating of the Stent Graft-effects on Platelets, Coagulation and Complement Activation," Biomaterials, 22: 349-355 (2001).
Chua et al., "Effect of microneedles shape on skin penetration and minimally invasive continuous glucose monitoring in vivo," Sensors and Actuators A: Physical, 203:373-381 (2013).
Cini et al., "Step-by-step assembly of self-patterning polyelectrolyte films violating (almost) all rules of layer-by-layer deposition," J Am Chem Soc, 132(24):8264-5 (2010).
Clark et al., "Selective Deposition in Multilayer Assembly: SAMs as Molecular Templates," Supramolecular Science, 4: 141 (1997).
Corkery et al., "Epidermal Growth Factor Receptor as a Potential Therapeutic Target in Triple-negative Breast Cancer," Annals of Oncology, 20: 862-867 (2009).
Correa et al., "Tuning Nanoparticle Interactions with Ovarian Cancer through Layer-by-Layer Modification of Surface Chemistry," ACS Nano, 14: 2224-2237 (2020) : Supporting Information.
Correa et al., "Tuning Nanoparticle Interactions with Ovarian Cancer through Layer-by-Layer Modification of Surface Chemistry," ACS Nano, 14: 2224-2237 (2020).
Cotten et al., "Receptor-Mediated Transport of DNA into Eukaryotic Cells," Methods Enzym, 217: 618-644 (1993).
Crane et al., Cyclodextrin Inclusion Complexes with a Solvatochromic Fluorescent Probe, Journal of Chemical Education, 79(10): 1261-1263 (2002).
Croce, "Causes and consequences of microRNA dysregulation in cancer," Nat. Rev. Genet., 10(10):704-714 (2009).
Crouzier et al., "Ion pairing and hydration in polyelectrolyte multilayer films containing polysaccharides," Biomacromolecules, 10(2):433-42 (2009).
Crouzier et al., "The performance of BMP-2 loaded TCP/HAP porous ceramics with a polyelectrolyte multilayer film coating," Biomaterials, 32(30): 7543-7554 (2011).
Crowley et al., "Liquid biopsy: monitoring cancer-genetics in the blood," Nature Reviews Clinical Oncology, 10:472-484 (2013).
Crystal, "Transfer of Genes to Humans: Early Lessons and Obstacles to Success," Science, 270: 404-410 (1995).
Dalby et al., "The control of human mesenchymal cell differentiation using nanoscale symmetry and disorder," Nat Mater, 6(12):997-1003 (2007).
Danese et al., "Circulating Nucleic Acids and Hemostasis: Biological Basis behind Their Relationship and Technical Issues in Assessment," Semin Thromb Hemost, 40:766-773 (2014).
Danhier et al., "PLGA-based nanoparticles: an overview of biomedical applications," J Control Release, 161(2): 505-522 (2012).
Danusso et al., "Synthesis of Tertiary Amine Polymers," Polymer, 11: 88-113 (1970).
Dash et al., "The influence of size and charge of chitosan/polyglutamic acid hollow spheres on cellular internalization, viability, and blood compatibility," Biomaterials, 31: 8188-8197 (2010).
Daubendiek et al., "Rolling-circle RNA-synthesis—circular oligonucleotides as efficient substrates for T7 RNA polymerase," J Am Chem Soc, 117:7818-7819 (1995).
Davis et al., " Evidence of RNAi in humans from systemically administered siRNA via targeted nanoparticles," Nature, 464: 1067-1070 (2010).
Davis et al., "Challenges and potential for RNA nanoparticles (RNPs)," J Biomed Nanotechnol, 5(1):36-44 (2009).
Davis et al., "Cyclodextrin-Based Pharmaceutics: Past, Present and Future," Nature Reviews, 3: 1023-1035 (2004).
De Jonge et al., "The osteogenic effect of electrosprayed nanoscale collagen/calcium phosphate coatings on titanium," Biomaterials, (9):2461-9 (2010).
Decher et al., "Buildup of Ultrathin Multilayer Films by a Self-Assembly Process, 1 Consecutive Adsorption of Anionic and Cationic Bipolar Amphiphiles on Charged Surfaces," Makromol Chem, Macro Mol Symp, 46: 321-327 (1991).
Decher et al., "Buildup of Ultrathin Multilayer Films by a Self-Assembly Process, II. Consecutive Adsorption of Anionic and Cationic Bipolar Amphilphiles and Polyelectrolytes on Charged Surfaces," Ber Bunsenges Phys Chem, 95(11): 1430-1434 (1991).
Decher et al., "Fuzzy Nanoassemblies: Toward Layer Polymeric Multicomposites," Science, 277: 1232-1237 (1997).
Decher et al., "Layer-by-layer assembled multicomposite Films," Current Opinion in Colloid & Interface Science, 3: 32-39 (1998).
Decher et al., "New Nanocomposite Films for Biosensors: Layer-by-layer Absorbed Films of Polyelectrolytes, Protein or DNA," Biosensors & Bioelectronics, 9: 677-684 (1994).

(56) References Cited

OTHER PUBLICATIONS

Delongchamp et al., "Fast Ion Conduction in Layer-By-Layer Polymer Films," Chem Mater, 15: 1165-1173 (2003).
Delongchamp et al., "High-Contrast Electrochromism and Controllable Dissolution of Assembled Prussian Blue/Polymer Nanocomposites," Adv Funct Mater, 14(3): 224-231 (2004).
Delongchamp, "High-Contrast Electrochromism from Layer-By-Layer Polymer Films," Chem Mater, 15: 1575-1586 (2003).
Demeneix et al., "The Proton Sponge: A Trick the Viruses did not Exploit," in ACS Conference Proceedings Series ; 146-151, Artificial self-assembling systems for gene delivery; 1995; Washington; DC.
Demidov et al., "Stability of peptide nucleic acids in human serum and cellular extracts," Biochem. Pharmacol., 48:1310-1313 (1994).
DeMuth et al., "Composite Dissolving Microneedles for Coordinated Control of Antigen and Adjuvant Delivery Kinetics in Transcutaneous Vaccination," Adv. Funct. Mater., 23:161-172 (2013).
DeMuth et al., "Implantable silk composite microneedles for programmable vaccine release kinetics and enhanced immunogenicity in transcutaneous immunization," Adv. Healthcare Mater., 3(1):47-58 (2014).
DeMuth et al., "Implantable Silk Composite Microneedles for Programmable Vaccine Release Kinetics and Enhanced Immunogenicity in Transcutaneous Immunization," Advance Healthcare Materials, 3(1): 47-58 (2014).
DeMuth et al., "Nano-layered microneedles for transcutaneous delivery of polymer nanoparticles and plasmid DNA," Adv Mater, 22(43):4851-6 (2010).
DeMuth et al., "Nano-layered Microneedles for Transcutaneous Delivery of Polymer Nanoparticles and Plasmid DNA," Adv. Mater., 22:4851-4856 (2010).
DeMuth et al., "Polymer multilayer tattooing for enhanced DNA vaccination," Nat Mater, 12(4): 367-376 (2013).
DeMuth et al., "Releasable Layer-by-Layer Assembly of Stabilized Lipid Nanocapsules on Microneedles for Enhanced Transcutaneous Vaccine Delivery," ACS Nano, 6(9):8041-8051 (2012).
DeMuth et al., "Vaccine delivery with microneedle skin patches in nonhuman primates," Nat. Biotechnol., 31(12):1082-1085 (2013).
Dent et al., "Triple-Negative Breast Cancer: Clinical Features and Patterns of Recurrence," Clinical Cancer Research, 13: 4429-4434 (2007).
Deshmukh et al., "Liposome and Polylysine Mediated Gene Transfer," New J Chem, 21: 113-124 (1997).
Diaz et al., "Antitumor and Antiangiogenic Effect of the Dual EGFR and HER-2 Tyrosine Kinase Inhibitor Lapatinib in a Lung Cancer Model," BMC Cancer, 10: 188 (2010).
Diegelman et al., "Generation of circular RNAs and trans-cleaving catalytic RNAs by rolling transcription of circular DNA oligonucleotides encoding hairpin ribozymes," Nucleic Acids Res, 26:3235-3241 (1998).
Dimitriou et al., "Bone regeneration: current concepts and future directions," BMC medicine, 9:66 (2011).
Dimitrova et al., "Sustained delivery of siRNAs targeting viral infection by cell-degradable multilayered polyelectrolyte films," PNAS, 105(42): 16320-16325 (2008).
Dixon, "Quartz crystal microbalance with dissipation monitoring: enabling real-time characterization of biological materials and their interactions," J Biomol Tech, 19(3):151-8 (2008).
Doh et al., "Aqueous-processible photoresist polymer for multiple protein patterning: Synthesis, characterization and application to T cell activation," Polymeric Materials Science and Engineering, 93:327-328 (2005).
Doh et al., "Photogenerated polyelectrolyte bilayers from an aqueous-processible photoresist for multicomponent protein patterning," J Am Chem Soc, 126: 9110-9171 (2004).
Dowben, "General Physiology: A Molecular Approach," Harper & Row Publishers, pp. 142-143 (1969).
Dubas et al., "Multiple Membranes from "True" Polyelectrolyte Multilayers," J Am Chem Soc, 123: 5368-5369 (2001).

Dubas et al., "Polyelectrolyte Multilayers Containing a Weak Polyacid: Construction and Deconstruction," Macromolecules, 34: 3736-3740 (2001).
Duek et al., "A Solid-State Electrochromic Device Based on Polyaniline, Prussian Blue and an Elastomeric Electrolyte," Advanced Materials, 5(9): 650-652 (1993).
Egholm et al., "PNA hybridizes to complementary oligonucleotides obeying the Watson-Crick hydrogen-bonding rules," Nature, 365:566-568 (1993).
Ekins et al., "24: Pathway Mapping Tools for Analysis of High Content Data," Methods in Molecular Biology, 356: 319-350 (2007).
Ekwueme et al., "Model-based estimates of risks of disease transmission and economic costs of seven injection devices in sub-Saharan Africa," Bulletin of the World Health Organization, 80:859-870 (2002).
El-Ghannam et al., "Model surfaces engineered with nanoscale roughness and RGD tripeptides promote osteoblast activity," J Biomed Mater Res, 68(4):615-27 (2004).
Elbakry et al., "Layer-by-layer assembled gold nanoparticles for siRNA delivery," Nano Lett, 9:2059-2064 (2009).
Elbashir et al., "Duplexes of 21-nucleotide RNAs mediate RNA interference in cultured mammalian cells," Nature, 411:494-498 (2011).
Elbert et al., "Self-assembly and Steric Stabilization at Heterogeneous, Biological Surfaces Using Absorbing Block Copolymers," Chemistry & Biology, 5(3): 177-183 (1998).
Ellis et al., "Electrochromism in the Mixed-Valence Hexacyanides. 1. Voltammetric and Spectral Studies of the Oxidation and Reduction of Thin Films of Prussian Blue," J Phys Chem, 85: 1225-1231 (1981).
European Search Report for EP Application No. 08771046.3 dated Oct. 22, 2012.
European Search Report for EP Application No. 11778208.6 dated May 20, 2014.
European Search Report for EP Application No. 12777399.2 dated Oct. 21, 2014.
European Search Report for EP Application No. 13781212.9 dated Aug. 18, 2015.
Facca et al., "Active multilayered capsules for in vivo bone formation," Proc Natl Acad Sci, 107(8): 3406-3411 (2010).
Feiler et al., "Adsorption and viscoelastic properties of fractionated mucin (BSM) and bovine serum albumin (BSA) studied with quartz crystal microbalance (QCM-D)," J Colloid Interface Sci, 315(2):475-81 (2007).
Ferruti et al., "Amphoteric Linear Poly(amido-amine)s as Endosomolytic Polymers: Correlation between Physicochemical and Biological Properties," Macromolecules, 33(21): 7793-7800 (2000).
Ferruti et al., "Linear Amino Polymers: Synthesis, Protonation and Complex Formation," Advances in Polymer Science, 58: 55-92 (1984).
Ferruti et al., "Recent Results on Functional Polymers and Macromonomers of Interest as Biomaterials or for Biomaterial Modification," Biomaterials, 15: 1235-1241 (1994).
Ferruti et al., "Synthesis, Characterisation and Antitumour Activity of Platinum (II) Complexes of Novel Functionalised Poly(amidoamine)s," Macromol Chem Phys, 200: 1644-1654 (1999).
Ferruti et al., "Synthesis, Physico-Chemical Properties and Biomedical Applications of Poly(aminoamine)s," Polymer, 26: 1336 (1985).
Fire et al., "Potent and Specific Genetic Interference by Double-Stranded RNA in Caenorhabditis Elegans," Nature, 391: 806-811 (1998).
Fitzgerald et al., "Systems Biology and Combination Therapy in the Quest for Clinical Efficacy," Nature Chemical Biology, 2(9): 458-466 (2006).
Fleischhacker et al., "Circulating nucleic acids (CNAs) and cancer—A survey," Biochimica et Biophysica Acta (BBA)—Reviews on Cancer, 1775:181-232 (2007).
Flessner et al., "Degradable Polyelectrolyte Multilayers that Promote the Release of siRNA," Langmuir, 27(12): 7868-7876 (2011).
Freiberg et al., "Polymers Microspheres for Controlled Drug Release," Int J Pharm, 282: 1-18 (2004).

(56) References Cited

OTHER PUBLICATIONS

Friedman, "Human Gene Therapy—An Immature Genie, but Certainly Out of the Bottle," Nature Med, 2: 144-147 (1996).
Gao et al., "Layer-by-layer Electrodeposition of Redox Polymers and Enzymes on Screen-printed Carbon Electrodes for the Preparation of Reagentless Biosensors," ChemComm 7(1): 30-1 (2003).
Gaudet et al., "A Compendium of Signals and Responses Triggered by Prodeath and Prosurvival Cytokines," Molecular & Cellular Proteomics, 4: 1569-1590 (2005).
Gemici et al., "Hydrothermal treatment of nanoparticle thin films for enhanced mechanical durability," Langmuir, 24(5):2168-77 (2008).
Gerasimov et al., "Cytosolic Drug Delivery Using pH-and Light-Sensitive Liposomes," Adv Drug Delivery Rev, 38: 317-338 (1999).
Giljohann et al., "Gene regulation with polyvalent siRNA-nanoparticle conjugates," J Am Chem Soc, 131: 2072-2073 (2009).
Gill et al., "Coated microneedles for transdermal delivery," J Controlled Release, 117:227-237 (2007).
Gill et al., "Cutaneous vaccination using microneedles coated with hepatitis C DNA vaccine," Gene Ther, 17:811-814 (2010).
Giudice et al., "Needle-free vaccine delivery," Adv Drug Delivery Rev, 58(1): 68-89 (2006).
Glenn et al., "Transcutaneous immunization and immunostimulant strategies: capitalizing on the immunocompetence of the skin," Expert Rev Vaccines, 2:253 (2003).
Gonzalez et al., "New Class of Polymers for the Delivery of Macromolecular Therapeutics," Bioconjugate Chem, 10: 1068-1074 (1999).
Grabow et al., "Loaded-up Microsponges," Nature Materials, 11(4): 268-269 (2012).
Grabowski et al., "Bone graft and bone graft substitutes in spine surgery: current concepts and controversies," J Am Acad Orthop Sur, 21(1): 51-60 (2013).
Graham et al., "Phase inversion dynamics of PLGA solutions related to drug delivery," J Controlled Release 58(2): 233-245 (1999).
Grayson et al., "Electronic MEMS for Triggered Drug Delivery," Advanced Drug Delivery Reviews, 56: 173-184 (2004).
Greenland et al., "Beta-amino ester polymers facilitate in vivo DNA transfection and adjuvant plasmid DNA immunization," Molecular Therapy, 12(1): 164-170 (2005).
Grewal et al., "Heterochromatin and epigenetic control of gene expression," Science, 301:798-802 (2003).
Guo, "RNA nanotechnology: engineering, assembly and applications in detection, gene delivery and therapy," J. Nanosci Nanotechnol, 5:1964-1982 (2005).
Guo, "Rolling Circle Transcription of Tandem siRNA to Generate Spherulitic RNA Nanoparticles for Cell Entry," Molecular Therapy, Nucleic Acids, 1: 3162-2531 (2012).
Guo, "The emerging field of RNA nanotechnology," Nature Nanotechnol, 5:833-842 (2010).
Habib et al., "A Tungsten-trioxide/prussian Blue Complementary Electrochromic Cell with a Polymer Electrolyte," Journal of Applied Electrochemistry, 21: 203-207 (1991).
Habib et al., "Effect of Temperature on a Complementary W03-Prussian Blue Electrochromic System," J Electrochem Soc, 139(8): 2155-2157 (1992).
Haensler et al., "Polyamidoamine Cascade Polymers Mediate Efficient Transfection of Cells in Culture," Bioconjugate Chem, 4: 372-379 (1993).
Halvorsen et al., "Profiling of microRNAs in tumor interstitial fluid of breast tumors—a novel resource to identify biomarkers for prognostic classification and detection of cancer," Mol. Oncol., 11:220-234 (2017).
Hammond et al., "Formation of Polymer Microstructures by Selective Deposition of Polyion Multilayers Using Patterned Self-Assembled Monolayers as a Template," Macromolecules, 28: 7569-7571 (1995).
Hammond, "Building biomedical materials layer-by-layer," Mater Today, 15(5): 196-206 (2012).
Hammond, "Form and Function in Multilayer Assembly: New Applications at the Nanoscale," Adv Mater, 16: 1271-1293 (2004).
Hanahan et al., "The Hallmarks of Cancer," Cell, 100: 57-70 (2000).
Hanes et al., "New Advances in Microsphere-Based Single-Dose Vaccines," Adv Drug Delivery Rev, 28: 97-119 (1997).
Hansen et al., "Re-Examination and Further Development of a Precise and Rapid Dye Method for Measuring Cell Growth/Cell Kill," Immunol Methods, 119: 203-210 (1989).
Haq et al., "Clinical administration of microneedles: Skin puncture, pain and sensation," Biomed Microdevices, 11:35 (2009).
Harper et al., "The DNA Damage Response: Ten Years After," Molecular Cell, 28(5): 739-745 (2007).
Haynie et al., "Protein-inspired multilayer nanofilms: science, technology and medicine," Nanomedicine, 2(3):150-7 (2006).
Hehrlein et al., "Drug-eluting Stent: The "Magic Bullet" for Prevention of Restenosis?" Basic Res Cardiol, 97: 417-423 (2002).
Helfrich et al., "Antitumor Activity of the Epidermal Growth Factor Receptor (EGFR) Tyrosine Kinase Inhibitor Gefitinib (ZD1839, Iressa) in Non-Small Cell Lung Cancer Cell Lines Correlates with Gene Copy Number and EGFR Mutations but not EGFR Protein Levels," Clinical Cancer Research, 12: 7117-7125 (2006).
Heller, "Redox Hydrogel-based Electrochemical Biosensors," Biosensors, Second Edition, edited by Jonathan Cooper, Anthony Cass, OUP Oxford, pp. 1-18 (2004).
Hendrix, "Bacteriophage DNA packaging: RNA gears in a DNA transport machine," Cell, 94(2): 147-50 (1998).
Hill et al., "In Vitro Cytotoxicity of Poly(amidoamine)s: Relevance to DNA Delivery," Biochim Biophys Acta, 1427: 161-174 (1999).
Hillberg et al., "Effect of genipin cross-linking on the cellular adhesion properties of layer-by-layer assembled polyelectrolyte films," Biomaterials, 30(27):4463-70 (2009).
Hope et al., "Cationic Lipids, Phosphatidylethanolamine and the Intracellular Delivery of Polymeric, Nucleic Acid-Based Drugs (Review)," Molecular Membrane Biology, 15: 1-14 (1998).
Hossfeld et al., "Bioactive Coronary Stent Coating Based on Layer-By-Layer Technology for SiRNA Release," Acta Biomaterialia, 9(5): 6741-6752 (2013).
Hu et.al., "Regulation of Silk Material Structure by Temperature-Controlled Water Vapor Annealing," Biomacromolecules, 12: 1686-1696 (2011).
Huang et al., "Liquid biopsy utility for the surveillance of cutaneous malignant melanoma patients," Mol. Oncol., 10:450-463 (2016).
Hyrup et al., "Peptide Nucleic Acids (PNA): Synthesis, properties and potential applications," Bioorganic & Medicinal Chemistry, 4(1):5-23 (1996).
International Preliminary Examination Report for International Application No. PCT/US2002/34191, dated Sep. 11, 2003.
International Preliminary Report on Patentability and Written Opinion for International Application No. PCT/US2009/054011, dated Feb. 22, 2011.
International Preliminary Report on Patentability and Written Opinion for International Application No. PCT/US2012/035689, dated Oct. 29, 2013.
International Preliminary Report on Patentability for International Application No. PCT/US08/66948, dated Dec. 17, 2009.
International Preliminary Report on Patentability for International Application No. PCT/US2006/004295, dated Aug. 7, 2007.
International Preliminary Report on Patentability for International Application No. PCT/US2007/069937, dated Dec. 3, 2008.
International Preliminary Report on Patentability for International Application No. PCT/US2007/69964, dated Dec. 3, 2008.
International Preliminary Report on Patentability for International Application No. PCT/US2011/035057, dated Nov. 6, 2012.
International Preliminary Report on Patentability for International Application No. PCT/US2012/035692, dated Oct. 29, 2013.
International Preliminary Report on Patentability for International Application No. PCT/US2013/022430, dated Jul. 22, 2014.
International Preliminary Report on Patentability for International Application No. PCT/US2013/037868, dated Nov. 20, 2014.
International Preliminary Report on Patentability for International Application No. PCT/US2013/37869, dated Nov. 6, 2014.
International Preliminary Report on Patentability for International Application No. PCT/US2016/068823 dated Jul. 12, 2018.

(56) References Cited

OTHER PUBLICATIONS

International Preliminary Report on Patentability for PCT/US2013/064530, entitled "Multilayer Compositions, Coated Devices and Use Thereof", dated Apr. 8, 2014.
International Preliminary Report on Patentability for PCT/US2013/066980, dated May 7, 2015.
International Search Report and Written Opinion for International Application No. PCT/US2007/69964, dated Oct. 29, 2007.
International Search Report and Written Opinion for International Application No. PCT/US2016/068823 dated Mar. 10, 2017.
International Search Report and Written Opinion for International Application No. PCT/US2018/014449 dated May 4, 2018.
International Search Report and Written Opinion for International Application No. PCT/US2018/058177 dated Feb. 15, 2019.
International Search Report and Written Opinion for International Application No. PCT/US2020/035327 dated Nov. 16, 2020.
International Search Report for International Application No. PCT/US08/66948, dated Aug. 29, 2008.
International Search Report for International Application No. PCT/US11/35057, dated Feb. 8, 2012.
International Search Report for International Application No. PCT/US2002/34191, dated Jan. 17, 2003.
International Search Report for International Application No. PCT/US2006/004295, dated Oct. 2, 2006.
International Search Report for International Application No. PCT/US2007/069937, dated Aug. 13, 2008.
International Search Report for International Application No. PCT/US2009/054011, dated Nov. 24, 2010.
International Search Report for International Application No. PCT/US2011/035057, dated Feb. 8, 2012.
International Search Report for PCT/US2012/035689, entitled: "Coating Compositions, Methods And Coated Devices," dated Jul. 31, 2012.
International Search Report for PCT/US2012/35692, entitled: "Coating Compositions, Methods And Coated Devices," dated Oct. 5, 2012.
International Search Report for PCT/US2013/022430, entitled: "Compositions And Methods For Coating," dated May 15, 2013.
International Search Report for PCT/US2013/066980, entitled: "Devices and Methods for Layer-by-Layer Assembly," dated Apr. 30, 2014.
International Search Report for PCT/US2013/37868, entitled: "Compositions And Methods Of Treatment Of Drug Resistant Cancers," dated Sep. 6, 2013.
International Search Report for PCT/US2013/37869, entitled: "Stable Layer-By-Layer Coated Particles," dated Sep. 13, 2013.
International Search Report for PCT/US2014/018284, entitled: "Nucleic Acid Particles, Methods And Use Thereof," dated Jul. 30, 2014.
International Search Report for PCT/US2014/022107, entitled: "Compositions and Methods For Nucleic Acid Delivery," dated Jun. 5, 2014.
International Search Report for PCT/US2014/057496, entitled: Biodegradable Layer-by-Layer (LbL) Films for Cell Capture and Release, dated Jan. 8, 2015.
Isakoff et al., "Triple Negative Breast Cancer: Role of Specific Chemotherapy Agents," Cancer Journal, 16(1): 53-61 (2010).
Itaya et al., "Prussian-blue-modified Electrodes: An Application for a Stable Electrochromic Display Device," J Appl Phys, 53: 804-805 (1982).
Ito et al., "Therapeutic Drug Monitoring of Vancomycin in Dermal Interstitial Fluid Using Dissolving Microneedles," Inter. J. Med. Sci., 13(4):271-276 (2016).
Janes et al., "A Systems Model of Signaling Identifies a Molecular Basis Set for Cytokine-Induced Apoptosis," Science, 310: 1646-1653 (2005).
Janes et al., "Cytokine-Induced Signaling Networks Prioritize Dynamic Range over Signal Strength," Cell, 135: 343-354 (2008).
Jelle et al., "Transmission Spectra of an Electrochromic Window Consisting of Polyaniline, Prussian Blue and Tungsten Oxide," Electrochimica Acta, 38(11): 1497-1500 (1993).

Jensen et al., "Characterization of Alginates by Nuclear Magnetic Resonance (NMR) and Vibrational Spectroscopy (IR, NIR, Raman) in Combination with Chemometrics," Methods Mol. Biol., 1308:347-363 (2015).
Jessel et al., "Multiple and Time-scheduled in Situ DNA Delivery Mediated by ?-cyclodextrin Embedded in a Polyelectrolyte Multilayer," Proc Nat Acad Sci, 103(23): 8618-8621 (2006).
Jewell et al., "Multilayered polyelectrolyte assemblies as platforms for the delivery of DNA and other nucleic acid-based therapeutics" Adv. Drug Delivery Rev. 60: 979 (2008).
Jewell et al., "Multilayered polyelectrolyte films promote the direct and localized delivery of DNA to cells," J Controlled Release, 106: 214-223 (2005).
Jewell et al., "Release of Plasmid DNA from Intravascular Stents Coated with Ultrathin Multilayered Polyelectrolyte Films," Biomacromolecules, 7: 2483-2491 (2006).
Jiang et al., "Selective Deposition in Layer-by-Layer Assembly: Functional Graft," Langmuir, 16: 8501-8509 (2000).
Jin et al., "Electrospinning Bombyx mori Silk with Poly(ethylene oxide)," Biomacromolecules, 3: 1233-9 (2002).
Johannsmann et al., "Effect of sample heterogeneity on the interpretation of QCM(-D) data: comparison of combined quartz crystal microbalance/atomic force microscopy measurements with finite element method modeling," Anal Chem, 80(23): 8891-8899 (2008).
Johansen et al., "Antigen kinetics determines immune reactivity," Proc Natl Acad Sci U.S. A., 105: 5189-5194 (2008).
John Wiley and Sons, Lysozyme: Substrate Structure, accessed Oct. 15, 2014, p. 1.
Johnston et al., "Targeting Cancer Cells: Controlling the Binding and Internalization of Antibody-Functionalized Capsules," ACS Nano, 6(8): 6667-6674 (2012).
Kabanov et al., "DNA Complexes with Polycations for the Delivery of Genetic Material into Cells," Bioconjugate Chem, 6: 7-20 (1995).
Kang et al., "Inhibition of EGFR Signaling Augments Oridonin-induced Apoptosis in Human Laryngeal Cancer Cells via Enhancing Oxidative Stress Coincident with Activation of Both the Intrinsic and Extrinsic Apoptotic Pathways," Cancer Letters, 294: 147-158 (2010).
Kargina et al., "Self-Splitting Water-Soluble Ionogenic Polymers" Vysokomol. Soedin. Seriya A, 28: 1139-1144, 1986. (with English abstract).
Kargina, O.V., "Samorasscheplyayuschiyesya Vodorastvorimye Ionogennye Polymery," (English Abstract).
Kearney et al., "Macroscale delivery systems for molecular and cellular payloads," Nat Mater, 12(11): 1004-1017 (2013).
Keselowsky et al., "Integrin $\alpha_5$ controls osteoblastic proliferation and differentiation responses to titanium substrates presenting different roughness characteristics in a roughness independent manner," J Biomed Mater Res A, 80(3): 700-710 (2007).
Khan et al., "Tissue engineering of bone: material and matrix considerations," J Bone Joint Surg, 90(Suppl 1): 36-42 (2008).
Khopade et al., "Electrostatically Assembled Polyelectrolyte/Dendrimer Multilayer Films as Ultrathin Nanoreservoirs," Nano Letters, 2: 415 (2002).
Kim et al., "Enhanced memory responses to seasonal H1N1 influenza vaccination of the skin with the use of vaccine-coated microneedles," J Infect Dis, 201(2): 190-198 (2010).
Kim et al., "Hydrogen-Bonding Layer-by-Layer-Assembled Biodegradable Polymeric Micelles as Drug Delivery Vehicles from Surfaces," ACS Nano, 2(2): 386-392 (2008).
Kim et al., "MAD (multiagent delivery) nanolayer: delivering multiple therapeutics from hierarchically assembled surface coatings," Langmuir, 25(24): 14086-14092 (2009).
Kim, "Recent Advances in Understanding the Cell Death Pathways Activated by Anticancer Therapy," Cancer, 103(8): 1551-1560 (2005).
Kinsella et al., "BMP-2-mediated regeneration of large-scale cranial defects in the canine: an examination of different carriers," Plast Reconstr Surg, 127(5): 1865-1873 (2011).
Klopman et al., "Recent Methodologies for the Estimation of N-Octanol/Water Partition Coefficients and their Use in the Prediction of Membrane Transport Properties of Drugs," Mini-Reviews in Medicinal Chemistry, 5: 127-133 (2005).

(56) References Cited

OTHER PUBLICATIONS

Knapp et al., "Crystal Structure of the Human Ecto-50-Nucleotidase (CD73): Insights into the Regulation of Purinergic Signaling," Structure, 20: 2161-2173 (2012).
Kolluru et al., "Recruitment and Collection of Dermal Interstitial Fluid Using a Microneedle Patch," Adv Healthc Mater., 8(3):e1801262 (2019).
Krasnici et al., "Effect of the Surface Charge of Liposomes on Their Update by Angiogenic Tumor Vessels," Int J Cancer, 105: 561-567 (2003).
Krebs et al., "The formation of spherulites by amyloid fibrils of bovine insulin," Proc Natl Acad Sci USA, 101: 14420-14424 (2004).
Krogman et al., "Industrial-scale spray layer-by-layer assembly for production of biomimetic photonic systems," Bioinspiration & Biomimetics, 8(4): 045005 (2013).
Krogman et al., "Spraying asymmetry into functional membranes layer-by-layer," Nat Mater, 8: 512-518 (2009).
Kuchler-Bopp et al., "Nanostructured hybrid materials for bone-tooth unit regeneration," Open Journal of Regenerative Medicine, 2(1): 47-52 (2013).
Kukowska-Latallo et al., "Efficient Transfer of Genetic Material into Mammalian Cells Using Starburst Polyamidoamine Dendrimers," Proc Nat Acad Sci USA, 93: 4897-4902 (1996).
Kumar et al., "Patterning Self-Assembled Monolayers: Applications in Materials Science," Langmuir, 10: 1498-1511 (1994).
Kwon et al., "Pseudopoly(amino acids): A Study of the Synthesis and Characterization of Poly(trans-4-hydroxy-N-acyi-L-proline esters)," Macromolecules, 22: 3250-3255 (1989).
Landes et al., "Maxillary and mandibular osteosyntheses with PLGA and P(L/DL)LA implants: A 5-year inpatient biocompatibility and degradation experience," Plastic and Reconstructive Surgery, 117(7): 2347-2360 (2006).
Langer, "Biomaterials in Drug Delivery and Tissue Engineering: One Laboratory's Experience," Acc Chem Res, 33: 94-101 (2000).
Langer, "Selected Advances in Drug Delivery and Tissue Engineering," J Control Release, 62: 7-11 (1999).
Lavan et al., "Small-scale Systems for in vivo Drug Delivery," Nature Biotechnology, 21(10): 1184-1191 (2003).
Lavos-Valereto et al., "In vitro and in vivo biocompatibility testing of Ti—6Al—7Nb alloy with and without plasma-sprayed hydroxyapatite coating," J Biomed Mater Res, 58(6):727-733 (2001).
Lawrence et al., "Bioactive Silk Protein Biomaterial Systems for Optical Devices," Biomacromolecules, 9(4): 1214-1220 (2008).
Lawrence et al., "Processing methods to control silk fibroin film biomaterial features," Journal of Material Sciences, 43: 6967-6985 (2008).
Lee et al., "Gold, poly(β-amino ester) nanoparticles for small interfering RNA delivery," Nano Lett, 9: 2402-2406 (2009).
Lee et al., "Growth factor delivery-based tissue engineering: general approaches and a review of recent developments," Journal of The Royal Society Interface, 8(55): 153-170 (2011).
Lee et al., "Self-assembled RNA Interference Microsponges for Efficient siRNA Delivery," Nature Materials, 11(4): 316-322 (2012).
Leguen et al., "Bioactive coatings based on polyelectrolyte multilayer architectures functionalized by embedded proteins, peptides or drugs," Biomol Eng, 24(1): 33-41 (2007).
Liang et al., "The minimal functional sequence of protamine," Biochem Biophys Res Commun, 336(2): 653-659 (2005).
Liao et al., "Response of rat osteoblast-like cells to microstructured model surfaces in vitro," Biomaterials, 24(4): 649-654 (2003).
Lichter et al., "Recent Advances in Radiation Oncology," New England Journal of Medicine, 332(6): 371-379 (1995).
Lieschke et al., "Bioactive murine and human interleukin-12 fusion proteins which retain antitumor activity in vivo," Nat Biotech 15:35-40 (1997).
Lim et al., "A Self-Destroying Polycationic Polymer: Biodegradable Poly(4-Hydroxy-L-proline Ester)," J Am Chem Soc, 121: 5633-5639 (1999).
Lim et al., "Cationic Hyperbranched Poly(amino ester): A Novel Class of DNA Condensing Molecule with Cationic Surface, Biodegradable Three-Dimensional Structure, and Tertiary Amine Groups in the Interior," J Am Chem Soc, 123: 2460-2461 (2001).
Lim et al., "Development of a Safe Gene Delivery System Using Biodegradable Polymer, Poly [?-(4-Aminobutyl-L-glycolic Acid]," J Am Chem Soc, 122: 6524-6525 (2000).
Lin et al., "PEG hydrogels for the controlled release of biomolecules in regenerative medicine," Pharmaceutical Research, 26(3): 631-643 (2009).
Linhardt et al., "Free-Radical Synthesis of Poly(2-Ethylacrylic Acid) Fractions of Low Polydispersity: Effects of Molecular Weight and Polydispersity on the pH-Dependent Conformational Transition in Aqueous Solution," Macromolecules, 32: 4457-4459 (1999).
Linhardt et al., "pH-Induced Fusion and Lysis of Phosphatidylcholine Vesicles by Hydrophobic Polyelectrolyte Poly(2-ethylacrylic Acid)," Langmuir, 16: 122-127 (2000).
Liu et al., "Porous polymer microneedles with interconnecting microchannels for rapid fluid transport," RSC Adv., 6:48630-48635 (2016).
Liu, "Ultrathin Multilayered Films that Promote the Release of Two DNA Constructs with Separate and Distinct Release Profiles," Adv Mater, 20: 4148-4153 (2008).
Livingstone et al., "Theoretical Property Predictions," J Curr Top Med Chem, 3: 1171-1192 (2003).
Lo et al., "Fabrication of controlled release biodegradable foams by phase separation," Tissue Eng, 1(1): 15-28 (1995).
Lopez et al., "Gefitinib Inhibition of Drug Resistance to Doxorubicin by Inactivating ABCG2 in Thyroid Cancer Cell Lines," Archives of Otolaryngology—Head & Neck Surgery, 133(10): 1022-1027 (2007).
Lu et al., "MicroRNA expression profiles classify human cancers," Nature, 435:834-838 (2005).
Luo et al., "Synthetic DNA Delivery Systems," Nat Biotechnol, 18: 33-37 (2000).
Lynn et al., "Accelerated Discovery of Synthetic Transfection Vectors: Parallel Synthesis and Screening of a Degradable Polymer Library," Journal of the American Chemical Society, 123: 8155-8156 (2001).
Lynn et al., "Construction of Degradable Thin Films via Layer-by-Layer Deposition of Polyelectrolytes: Fabrication, Characterization, and Application to Controlled Release," MIT Proposal (2001).
Lynn et al., "Degradable Poly(Beta-amino esters): Synthesis, Characterization, and Self-Assembly with Plasmid DNA," J Am Chem Soc, 122: 10761-10768 (2000).
Lynn et al., "pH-Responsive Polymer Microspheres: Rapid Release of Encapsulated Material Within the Range of Intracellular pH," Angewandte Chemie International Edition, 40: 1707-1710 (2001).
Lynn, "Peeling Back the Layers: Controlled Erosion and Triggered Disassembly of Multilayered Polyelectrolyte Thin Films," Adv Mater, 19: 4118-4130 (2007).
Ma et al., "Collagen/chitosan porous scaffolds with improved biostability for skin tissue engineering," Biomaterials, 24: 4833-4841 (2003).
MacBeath, "Protein Microarrays and Proteomics," Nature Genetics Supplement, 32: 526-532 (2002).
Macdonald et al., "Release of a model protein from biodegradable self assembled films for surface delivery applications," J Controlled Release, 131(3): 228-234 (2008).
MacDonald et al., "Tissue Integration of Growth Factor-Eluting Layer-by-Layer Polyelectrolyte Multilayer Coated Implants," Biomaterials, 32(5): 1446-1453 (2010).
Machine Translation of CN1679518A, 8 pages, publication date of CN1679518A is Oct. 2005. Translation was performed on Jul. 24, 2015.
Mandal et al. "Cell and fluid sampling microneedle patches for monitoring skin-resident immunity." Science Translational Medicine 10(467):eaar2227 (2018).
Mansouri et al., "Modulating the release kinetics through the control of the permeability of the layer-by-layer assembly: a review," Expert Opin Drug Deliv, 6(6): 585-597 (2009).
Martin et al., "Solubility and Kinetic Release Studies of Naproxen and Ibuprofen in Soluble Epichlorohydrin-β-cyclodextrin Polymer," Supramolecular Chemistry, 18(8): 627-631 (2006).

(56) References Cited

OTHER PUBLICATIONS

Martinez et al., "Single-stranded antisense siRNAs guide target RNA cleavage n RNAi," Cell, 110: 563-574 (2002).

Martino et al., "Engineering the growth factor microenvironment with fibronectin domains to promote wound and bone tissue healing," Sci Transl Med, 3(100): 100ra189 (2011).

Mathiowitz et al., "Polyanhydride Microspheres as Drug Carriers I. Hot-Melt Microencapsulation," J Controlled Release, 5: 13-22 (1987).

Mathiowitz et al., "Polyanhydride Microspheres as Drug Carriers II. Microencapsulation," J Appl Polymer Sci, 35: 755-774 (1988).

Mehrotra et al., "Time Controlled Protein Release from Layer-by-Layer Assembled Multilayer Functionalized Agarose Hydrogels," Adv Funct Mater, 20(2): 247-258 (2010).

Meinel et al., "Silk based biomaterials to heal critical sized femur defects," Bone, 39(4): 922-31 (2006).

Meltzer, "Small RNAs with big impacts," Nature, 435:745-746 (2005).

Mendelsohn et al., "Rational design of cytophilic and cytophobic polyelectrolyte multilayer thin films," Biomacromolecules, 4(1): 96-106 (2003).

Merriam-Webster, "Definition of peel," merriam-webster.com (Accessed Dec. 18, 2018).

Metcalf et al., "Amplification-Free Detection of Circulating microRNA Biomarkers from Body Fluids Based on Fluorogenic Oligonucleotide-Templated Reaction between Engineered Peptide Nucleic Acid Probes: Application to Prostate Cancer Diagnosis," Anal. Chem., 88:8091-8098 (2016).

Michel et al., "Printing Meets Lithography: Soft Approaches to High-Resolution Patterning," IBM Journal of Research and Development, 45(5): 697-719 (2001).

Mikos et al., "Preparation and Characterization of Poly(L-Lactic Acid) Foams," Polymer, 35(5): 1068-1077 (1994).

Mikszta et al., "Improved genetic immunization via micromechanical disruption of skin-barrier function and targeted epidermal delivery," Nat Med, 8: 415-419 (2002).

Milano et al., "EGFR-targeting Drugs in Combination with Cytotoxic Agents: From Bench to Bedside, a Contrasted Reality," British Journal of Cancer, 99: 1-5 (2008).

Miller et al., "Extraction and biomolecular analysis of dermal interstitial fluid collected with hollow microneedles," Commun. Biol., 1:173 (2018).

Miller et al., "Microneedle-based sensors for medical diagnosis," J. Mater. Chem. B, 4:1379-1383 (2016).

Miller, "Cationic Liposomes for Gene Therapy," Angew Chem Int Ed, 37: 1769-1785 (1998).

Mistry et al., "Tissue engineering strategies for bone regeneration," Regenerative Medicine II. Springer, 94: 1-22 (2005).

Mizushima et al., "Methods in Mammalian Autophagy Research," Cell, 140: 313-326 (2010).

Mok et al., "Multimeric small interfering ribonucleic acid for highly efficient sequence-specific gene silencing," Nature Mater, 9: 272-278 (2010).

Montesano et al., "Test for Malignant Transformation of Rat Liver Cells in Culture: Cytology, Growth in Soft Agar, and Production of Plasminogen Activator," Journal of the National Cancer Institute, 59(6): 1651-1658 (1977).

Moor et al., "Proteolytic Activity in Wound Fluids and Tissues Derived from Chronic Venous Leg Ulcers," Wound Repair and Regeneration, 17(6): 832-839 (2009).

Moran et al., "Mixed protein carriers for modulating DNA release," Langmuir, 25(17): 10263-10270 (2009).

Morgillo et al., "Antitumor Activity of Bortezomib in Human Cancer Cells with Acquired Resistance to Anti-Epidermal Growth Factor Receptor Tyrosine Kinase Inhibitors," Lung Cancer, 71: 283-290 (2011).

Moriguchi et al., "Synthesis of Ultrathin Films of Prussian Blue by Successive Ion Adsorption Technique," Chemistry Letters, 31(3): 310-311 (2002).

Morris et al., "Small interfering RNA-induced transcriptional gene silencing in human cells," Science, 305: 1289-1202 (2004).

Moskowitz et al., "The effectiveness of the controlled release of gentamicin from polyelectrolyte multilayers in the treatment of *Staphylococcus aureus* infection in a rabbit bone model," Biomaterials, 31(23): 6019-6030 (2010).

Mukerjee et al., "Microneedle array for transdermal biological fluid extraction and in situ analysis," Sens. Actuators A Phys., 114:267-275 (2004).

Mulligan, "The Basic Science of Gene Therapy," Science, 260: 926-932 (1993).

Murphy et al., "A Combinatorial Approach to the Delivery of Efficient Cationic Peptoid Reagents for Gene Delivery," Proc Natl Acad Sci USA, 95: 1517-1522 (1998).

Nagashima et al., "BCRP/ABCG2 levels account for the resistance to topoisomerase I inhibitors and reversal effects by gefitinib in non-small cell lung cancer," Cancer Chemotherapy and Pharmacology, 58: 594-600 (2006).

Nam et al., "Porous biodegradable polymeric scaffolds prepared by thermally induced phase separation," J Biomed Mater Res, 47(1): 8-17 (1999).

Neovius et al., "Craniofacial reconstruction with bone and biomaterials: review over the last 11 years," J Plast Reconstr Aesthet Surg, 63(10): 1615-1623 (2010).

Neve et al., "A Collection of Breast Cancer Cell Lines or the Study of Functionally Distinct Cancer Subtypes," Cancer Cell, 10: 515-527 (2006).

Nevins et al., "Platelet-derived growth factor stimulates bone fill and rate of attachment level gain: results of a large multicenter randomized controlled trial," J Periodontol, 76(12): 2205-2215 (2005).

Newman et al., "Natural Products as Sources of New Drugs over the Period 1981-2002," Journal of Natural Products, 66: 1022-1037 (2003).

Nguyen et al., "Extended Release Antibacterial Layer-by-Layer Films Incorporating Linear-Dendritic Block Copolymer Micelles," Chemistry of Materials, 19: 5524-5530 (2007).

Nielsen et al., "An Introduction to Peptide Nucleic Acid," Current Issues Molec. Biol., 1(2):89-104 (1999).

Niemiec et al., "Nanoheterogeneous multilayer films with perfluorinated domains fabricated using the layer-by-layer method," Langmuir, 26(14): 11915-11920 (2010).

Notice of Allowance and Fees Due for U.S. Appl. No. 14/811,263 dated Apr. 10, 2017.

O'Donnell et al., "Preparation of Microspheres by the Solvent Evaporation Technique," Adv Drug Delivery Rev, 28: 25-42 (1997).

Oh et al., "Stem cell fate dictated solely by altered nanotube dimension," Proc Natl Acad Sci U S A, 106(7): 2130-2135 (2009).

Okada, "One-and Three-Month Release Injectable Microspheres of the LH-RH Superagonist Leuprorelin Acetate," Adv Drug Delivery Rev, 28: 43-70 (1997).

Oliva et al., "Antiproliferative Drug-Eluting Stents: Systematic Review of the Benefits and Estimate of Economic Impact," Rev Esp Cardiol, 57(7): 617-628 (2004).

Ono et al., "A direct plasma assay of circulating microRNA-210 of hypoxia can identify early systemic metastasis recurrence in melanoma patients," Oncotarget, 6(9):7053-7064 (2015).

Ono et al., "Circulating microRNA Biomarkers as Liquid Biopsy for Cancer Patients: Pros and Cons of Current Assays," J. Clin. Med., 4:1890-1907 (2015).

Pan et al., "Cancer Immunotherapy Using a Membrane-bound Interleakin-12 with B7-1 Transmembrane and Cytoplasmic Domains," Molecular Therapy, 20(5): 927-937 (2012).

Papanas et al., "Benefit-risk assessment of becaplermin in the treatment of diabetic foot ulcers," Drug Safety: An International Journal of Medical Toxicology and Drug Experience, 33(6): 455-461 (2010).

Pareta et al., "An understanding of enhanced osteoblast adhesion on various nanostructured polymeric and metallic materials prepared by ionic plasma deposition," J Biomed Mater Res A, 92(3): 1190-1201 (2010).

(56) References Cited

OTHER PUBLICATIONS

Park et al., "Biodegradable polymer microneedles: fabrication, mechanics and transdermal drug delivery," J Controlled Release, 104: 51-66 (2005).
Park et al., "Osteoconductivity of hydrophilic microstructured titanium implants with phosphate ion chemistry," Acta Biomater, 5(6): 2311-2321 (2009).
Park et al., "Polymer microneedles for controlled-release drug delivery," Pharm Res, 23: 1008-1019 (2006).
Pasco et al., "Characterization of a Thermophilic L-glutamate Dehydrogenase Biosensor for Amperometric Determination of L-glutamate by Flow Injection Analysis," Biosensors & Bioelectronics, 14: 171-178 (1999).
Pashuck et al., "Designing Regenerative Biomaterial Therapies for the Clinic," Science Translational Medicine, 4(160): 160sr164 (2012).
Patil et al., "Surface-modified and internally cationic polyamidoamine dendrimers for efficient siRNA delivery," Bioconjug Chem, 19: 1396-1403 (2008).
Pawson et al., "Network Medicine," FEBS Letters, 582: 1266-1270 (2008).
Pearton et al., "Gene delivery to the epidermal cells of human skin explants using microfabricated microneedles and hydrogel formulations," Pharm Res, 25(2): 407-416 (2008).
Peer et al., "Selective gene silencing in activated leukocytes by targeting siRNAs to the integrin lymphocyte function-associated antigen-1," Proc Natl Acad Sci USA, 104(10): 4095-4100 (2007).
Peer et al., "Systemic leukocyte-directed siRNA delivery revealing cyclin D1 as an anti-inflammatory target," Science, 319: 627-630 (2008).
Peerce et al., "Polymer Films on Electrodes, Part III. Digital Simulation Model for Cyclic Voltammetry of Electroactive Polymer Film and Electrochemistry of Poly(vinylferrocene) on Platinum," J Electroanal Chem, 114: 89-115 (1980).
Perou et al., "Molecular Portraits of Human Breast Tumours," Nature, 406: 747-752 (2000).
Perry et al., "Nano- and Micropatterning of Optically Transparent, Mechanically Robust, Biocompatible Silk Fibroin Films," Advanced Materials, 20(16): 3070-3072 (2008).
Petrie et al., "The effect of integrin-specific bioactive coatings on tissue healing and implant osseointegration" Biomaterials, 29(19): 2849-2857 (2008).
Pfeifer et al., "Formulation and surface modification of poly(ester-anhydride) micro- and nanospheres," Biomaterials, 26: 117-124 (2005).
Picart et al., "Molecular Basis for the Explanation of the Exponential Growth of Polyelectrolyte Multilayers," Proc Natl Acad Sci, 99(20): 12531-12535 (2002).
Place et al., "Complexity in biomaterials for tissue engineering," Nat Mater, 8(6): 457-470 (2009).
Poerner et al., "Drug-coated Stent," Minimally Invasive Therapy & Allied Technologies, 11(4): 185-192 (2002).
Porcel et al., "From exponential to linear growth in polyelectrolyte multilayers" Langmuir, 22(9): 4376-4383 (2006).
Porcel et al., "Influence of the polyelectrolyte molecular weight on exponentially growing multilayer films in the linear regime," Langmuir, 23(4): 1898-1904 (2007).
Porter et al., "Bone tissue engineering: a review in bone biomimetics and drug delivery strategies," Biotechnology Progress, 25(6): 1539-1560 (2009).
Portin., "Layer-by-Layer Assembly of the Polyelectrolytes on Mesoporous Silicon Nanoparticles," Master's Thesis, University of Eastern Finland, Joensuu, Finland (2012).
Prausnitz et al., "Transdermal drug delivery," Nat Biotechnol, 26(11): 1261-1268 (2008).
Prausnitz, "Microneedles for transdermal drug delivery," Adv Drug Delivery Rev, 56: 581-587 (2004).
Presolski et al., "Copper-Catalyzed Azide-Alkyne Click Chemistry for Bioconjugation," Curr. Protoc. Chem. Biol., 3(4):153-162 (2011).
Pritchard et al., "Silk fibroin encapsulated powder reservoirs for sustained release of adenosine," Journal of Controlled Release, 144(2): 159-67 (2010).
Pruss-Ustun et al., "Introduction and methods: assessing the environmental burden of disease at national and local levels," Geneva, World Health Organization, 2003 (WHO Environmental Burden of Disease Series, No. 1).
Putnam et al., "Poly(4-hydroxy-L-proline ester): Low-Temperature Polycondensation and Plasmid DNA Complexation," Macromolecules, 32: 3658-3662 (1999).
Qiu et al., "Studies on the Drug Release Properties of Polysaccharide Multilayers Encapsulated Ibuprofen Microparticles," Langmuir, 17: 5375-5380 (2001).
Quan et al., "Stabilization of influenza vaccine enhances protection by microneedle delivery in the mouse skin," PLOS One, 4(9):e7152 (2009).
Quarles et al., "Distinct proliferative and differentiated stages of murine MC3T3-E1 cells in culture: an in vitro model of osteoblast development," J Bone Miner Res, 7(6):683-92 (1992).
Rainer et al., "Circulating Nucleic Acids and Critical Illness," Annals of the New York Science Academy of Science, 1075:271-277 (2006).
Rajan et al., "Electrochromism in the Mixed-Valence Hexacyanides. 2. Kinetics of the Reduction of Ruthenium Purple and Prussian Blue," J Phys Chem, 86: 4361-4368 (1982).
Ramaswamy et al., "Sphene ceramics for orthopedic coating applications: an in vitro and in vivo study," Acta Biomater, 5(8):3192-204 (2009).
Rao et al., "Poly(butanediol Spermate): A Hydrolytically Labile Polyester-Based Nitric Oxide Carrier," J Bioactive and Compatible Polymers, 14: 54-63 (1999).
Rausch-Fan et al., "Differentiation and cytokine synthesis of human alveolar osteoblasts compared to osteoblast-like cells (MG63) in response to titanium surfaces," Dent Mater, 24(1): 102-10 (2008).
Razzacki et al., "Integrated Microsystems for Controlled Drug Delivery," Advanced Drug Delivery Reviews, 56: 185-198 (2004).
Richards, et al., "R. Mode of DNA packing within bacteriophage heads," J Mol Biol, 78: 255-259 (1973).
Richert et al., "Cell interactions with polyelectrolyte multilayer films," Biomacromolecules, 3(6):1170-8 (2002).
Roach et al., "Interpretation of protein adsorption: surface-induced conformational changes," J Am Chem Soc, 127(22):8168-73 (2005).
Roach et al., "Modern biomaterials: a review—bulk properties and implications of surface modifications," J Mater Sci Mater Med, 18(7): 1263-77 (2007).
Roberts et al., "Preliminary Biological Evaluation of Polyamidoamine (P AMAM) Starburst TM Dendrimers," J Biomed Mater Res, 30: 53-65 (1996).
Robin et al., "The Color and Electronic Configurations of Prussian Blue," Inorg Chem, 1(2): 337-342 (1962).
Rockwood et al., "Materials fabrication from Bombyx mori silk fibroin," Nature Protocols, 6: 1612-1631 (2011).
Rohanizadeh et al., "Gelatin Sponges (Gelfoam®) as a scaffold for Osteoblasts", J Mater Sci Mater Med, 19:1173-1182 (2008).
Romanyuk et al., "Collection of Analytes from Microneedle Patches," Anal. Chem., 86:10520-10523 (2014).
Runge et al., "Paramagnetic NMR contrast agents. Development and evaluation," Investigative Radiology, 19(5): 408-415 (1984).
Rusnak et al., "Assessment of Epidermal Growth Factor Receptor (EGFR, ErbB1) and HER2 (ErbB2) Protein Expression Levels and Response to Lapatinib (Tykerb®, GW572016) in an Expanded Panel of Human Normal and Tumour Cell Lines," Cell Proliferation, 40: 580-594 (2007).
Sachs et al., "Casual Protein-Signaling Networks Derived from Multiparameter Single-Cell Data," Science, 308: 523-529 (2005).
Sadej et al., "Expression of ecto-5'-nucleotidase (eN, CD73) in cell lines from various stages of human melanoma," Melanoma Research, 16(3): 213-222 (2006).
Saha et al., "Designing synthetic materials to control stem cell phenotype," Curr Opin Chem Biol, 11(4):381-7 (2007).
Saito et al., "Epigenetic Activation of Tumor Suppressor MicroRNAs in Human Cancer Cells," Cell Cycle, 5(19):2220-2222 (2006).

(56) References Cited

OTHER PUBLICATIONS

Sallusto et al., "Central memory and effector memory T cell subsets: Function, generation, and maintenance," Annu Rev Immunol, 22:145-163, (2004).
Samant et al., "Mechanisms of sampling interstitial fluid from skin using a microneedle patch," Proc. Natl Acad. Sci. U.S.A., 115(18):4583-4588 (2018).
Samuel et al., "Osteoconductive protamine-based polyelectrolyte multilayer functionalized surfaces," Biomaterials, 32:1491-1502 (2011).
Sanford, "The Biolistic Process," Trends Biotechnol, 6: 299-302 (1988).
Santin et al., "In vitro evaluation of the inflammatory potential of the silk fibroin," Journal of Biomedical Materials Research, 46(3): 382-389 (1999).
Santini et al., "Microchips as Controlled Drug-Delivery Devices," Angew Chem Int Ed, 39: 2396-2407 (2000).
Santini et al., "Microchips for Drug Delivery," Abstracts of Meeting of the American Chemical Society, 219(174): U34-U34 (2000).
Sapi et al., "Ets-2 Transdominant Mutant Abolishes Anchorage-independent Growth and Macrophage Colony-stimulating Factor-stimulated Invasion by BT20 Breast Carcinoma Cells," Cancer Research, 58: 1027-1033 (1998).
Sato et al., "Layered Assemblies Composed of Sulfonated Cyclodextrin and Poly(allylamine)," Colloid & Polymer Science, 282: 287-290 (2004).
Sayers et al., "Peptide nucleic acid-templated selenocystine-selenoester ligation enables rapid miRNA detection," Chemical Science, 9: 896 (2018).
Schaefer et al., "In vivo nuclear magnetic resonance imaging of myocardial perfusion using the paramagnetic contrast agent manganese gluconate," Journal of The American College of Cardiology, 14(2): 472-480 (1989).
Schaffer et al., "Vector Unpacking as a Potential Barrier for Receptor-Mediated Polyplex Gene Delivery," Biotechnol Bioeng, 61: 598-606 (2000).
Schechter et al., "The Neu Oncogene: an Erb-8-related Gene Encoding a 185,000-Mr Tumour antigen," Nature, 312: 513-516 (1984).
Schlenoff, "Retrospective on the future of polyelectrolyte multilayers" Langmuir 25(24):14007-10 (2009).
Schmidt et al., "Electrochemically controlled swelling and mechanical properties of a polymer nanocomposite," ACS Nano, 3(8):2207-16 (2009).
Schmitz et al., "The Critical Size Defect as an Experimental-Model for Craniomandibulofacial Nonunions," Clinical Orthopaedics and Related Research, 205: 299-308 (1986).
Schuler, "Decomposable Hollow Biopolymer-Based Capsules," Biomacromolecules, 2: 921-926 (2001).
Schwarz et al., "Potential of chemically modified hydrophilic surface characteristics to support tissue integration of titanium dental implants," J Biomed Mater Res B Appl Biomater, 88(2):544-57 (2009).
Schweikl et al., "Triethylene Glycol Dimethacrylate Induces Large Deletions in the Hprt Gene of V79 Cells," Mutat Res, 438: 71-78 (1999).
Seeman, "Nanomaterials based on DNA," Annu Rev Biochem, 79:65-87 (2010).
Semple et al., "Rational design of cationic lipids for siRNA delivery," Nature Biotechnol, 28:172-176 (2010).
Sengupta et al., "Temporal Targeting of Tumor Cells and Neovasculature with a Nanoscale Delivery System," Nature, 436: 568-572 (2005).
Seo et al., "Effect of the layer-by-layer (LbL) deposition method on the surface morphology and wetting behavior of hydrophobically modified PEO and PAA LbL films," Langmuir, 24(15):7995-8000 (2008).
Sevecka et al., "State-based Discovery: A Multidimensional Screen for Small-Molecule Modulators of EGF Signaling," Nature Methods, 3(10): 825-831 (2006).
Seyhan et al., "RNA Interference from Multimeric shRNAs Generated by Rolling Circle Transcription," Oligonucleotides, 16(4): 353-363 (2006).
Shah et al., "Surface-Mediated Bone Tissue Morphogenesis from Tunable Nanolayered Implant Coatings," Science Translational Medicine, 5, 191ra83 (2013).
Shakeel et al., "Peptide nucleic acid (PNA)—a review," J. Chem. Technol. Biotechnol., 81:892-899 (2006).
Shi et al., "The epidermal growth factor tyrosine kinase inhibitor AG1478 and erlotinib reverse ABCG2-meditated drug resistance," Oncology Reports, 21: 483-489 (2008).
Shiratori et al., "pH-Dependent Thickness Behavior of Sequentially Adsorbed Layers of Weak Polyelectrolytes," Macromolecules, 33: 4213-4219 (2000).
Shkula et al., "Tunable Vancomycin Releasing Surfaces for Biomedical Applications," Small Nano Micro, 21(6): 2392-2404 (2010).
Shreve et al., "Monoclonal antibodies labeled with polymeric paramagnetic ion chelates," Magnetic Resonance in Medicine, 3(2): 336-340 (1986).
Shukla et al., "Controlling the release of peptide antimicrobial agents from surfaces," Biomaterials, 31(8):2348-2357 (2010).
Shutava et al., "Layer-by-Layer-Coated Gelatin Nanoparticles as a Vehicle for Delivery of Natural Polyphenols," ACS Nano, 3(7): 1877-85 (2009).
Singh et al., "Cationic Microparticles: A Potent Delivery System for DNA Vaccines," Proc Natl Acad Sci USA, 97: 811-816 (2000).
Siravegna et al., "Integrating liquid biopsies into the management of cancer," Nature Reviews Clinical Oncology, 14:531-548 (2017).
Sita-Lumsden et al., "Circulating microRNAs as potential new biomarkers for prostate cancer," British Journal of Cancer, 108:1925-1930 (2013).
Slamon et al., "Human Breast Cancer: Correlation of Relapse and Survival with Amplification of the HER-2/neu Oncogene," Science, 235: 177-182 (1987).
Smiell et al., "Efficacy and safety of becaplermin (recombinant human platelet-derived growth factor-BB) in patients with nonhealing, lower extremity diabetic ulcers: a combined analysis of four randomized studies," Wound Repair Regen, 7(5): 335-346 (1999).
Smith et al., "Enhancing DNA vaccination by sequential injection of lymph nodes with plasmid vectors and peptides," Vaccine, 27:2603-2615 (2009).
Smith et al., "Layer-by-Layer Platform Technology for Small-Molecule Delivery," Angew Chem Int Ed, 48: 8974-8977 (2009).
Smith et al., "Multivalent immunity targeting tumor-associated antigens by intra-lymph node DNA-prime ,peptide-boost vaccination," Cancer Gene Ther, 18:63-76 (2011).
Smith et al., "Silicon microneedle array for minimally invasive human health monitoring," Proc. SPIE 10491, Microfluidics, BioMEMS, and Medical Microsystems XVI, 1049102 (2018).
Sofia et al., "Functionalized silk-based biomaterials for bone formation," Journal of Biomedical Materials Research, 54(1): 139-148 (2001).
Song et al., "Growth of Endothelial Cell on the Surface of Intravascular Sent Material: Bionic Construction of Bioactive Extracellular Matrix," Journal of clinical Rehabilitative Tissue Engineering Research, 13(43): 8425-8431 (2009).
Sordella et al., "Gefitinib-Sensitizing EGFR Mutations in Lung Cancer Activate Anti-Apoptotic Pathways," Science, 305: 1163-1167 (2004).
Spicer et al., "Evaluation of bone regeneration using the rat critical size calvarial defect," Nature protocols, 7(10): 1918-1929 (2012).
Stevens, "Biomaterials for bone tissue engineering," Materials Today, 11(5): 18-25 (2008).
Strathmann, "Membrane separation processes: current relevance and future opportunities," AIChE Journal, 47(5): 1077-1087 (2001).
Stubbs et al., "The interaction of thrombin with fibrinogen," Eur J Biochem, 206:187-195 (1992).
Su et al., "Layer-by-layer-assembled multilayer films for transcutaneous drug and vaccine delivery," ACS Nano, 3: 3719-3729 (2009).
Subramanian et al., "Gene Set Enrichment Analysis: A Knowledge-based Approach for Interpreting Genome-wide Expression Profiles," Proc Natl Acad Sci USA, 102(43): 15545-15550 (2005).

(56) References Cited

OTHER PUBLICATIONS

Sulaiman et al., "Chemically Modified Hydrogel-Filled Nanopores: A Tunable Platform for Single-Molecule Sensing," Nano Lett., 18:6084-6093 (2018).
Sulaiman et al., "Hydrogel-coated microneedle arrays for minimally-invasive sampling and sensing of specific circulating nucleic acids from skin interstitial fluid," ACS Nano, 13(8): 9620-9628 (2019).
Sulaiman et al., "Subnanomolar Detection of Oligonucleotides through Templated Fluorogenic Reaction in Hydrogels: Controlling Diffusion to Improve Sensitivity," Angew. Chem. Int., 56:1-6 (2017).
Sullivan et al., "Dissolving polymer microneedle patches for influenza vaccination," Nat Med, 16:915-920 (2010).
Sullivan et al., "Minimally invasive protein delivery with rapidly dissolving polymer microneedles," Adv Mater, 20:933-938 (2008).
Sun et al., "Activation of Multiple Proto-oncogenic Tyrosine Kinases in Breast Cancer via Loss of the PTPN12 Phosphatase," Cell, 144: 703-718 (2011).
Swarup et al., "Circulating (cell-free) nucleic acids—A promising, non-invasive tool for early detection of several human diseases," FEBS Letters, 581:795-799 (2007).
Tang et al., "Adhesion and Endothelialization of Endothelial Cells on the Surface of Endovascular Stents by the Novel Rotational Culture of Cells," Applied Surface Science, 255: 315-319 (2008).
Tang et al., "In Vitro Gene Delivery by Degraded Polyamidoamine Dendrimers," Bioconjugate Chem, 7: 703-714 (1996).
Taratula et al. "Surface-engineered targeted PPI dendrimer for efficient intracellular and intratumoral siRNA delivery," J Control. Release, 140:284-293 (2009).
Tetko et al., "Virtual Computational Chemistry Laboratory-design and Description," Computer-Aided Mol Des, 19: 453-463 (2005).
Thompson et al., "Biochemical functionalization of polymeric cell substrata can alter mechanical compliance," Biomacromolecules, 7(6):1990-5 (2006).
Thompson et al., "Tuning compliance of nanoscale polyelectrolyte multilayers to modulate cell adhesion," Biomaterials, 26(34):6836-45 (2005).
Tijsterman et al., "The genetics of RNA silencing," Annu Rev Genet, 36:489-519 (2002).
Toniolo et al., "Protamines. II. Circular dichroism study of the three main components of clupeine," Biochim Biophys Acta, 576(2):429-39 (1979).
Trubetskoy et al., "Layer-by-layer deposition of oppositely charged polyelectrolytes on the surface of condensed DNA particles," Nucleic Acids Res, 27:3090-3095 (1999).
Turner et al., "ABCG2 Expression, Function, and Promoter Methylation in Human Multiple Myeloma," Blood, 108(12): 3881-3889 (2006).
Uhrich et al., "Polymeric Systems for Controlled Drug Release," Chem Rev, 99: 3181-3198 (1999).
Uhrich, "Hyperbranched Polymers for Drug Delivery," Trends Polym Sci, 5: 388-393 (1997).
Ulivi et al., "miRNAs as Non-Invasive Biomarkers for Lung Cancer Diagnosis," Molecules, 19:8220-8237 (2014).
Van de Wetering et al., "Structure-Activity Relationships of Water-Soluble Cationic Methacrylate/Methacrylamide Polymers for Nonviral Gene Delivery," Bioconjugate Chem, 10: 589-597 (1999).
Vazquez et al., "Variation of polyelectrolyte film stiffness by photo-cross-linking: a new way to control cell adhesion," Langmuir, 25(6):3556-63 (2009).
Ventrelli et al., "Microneedles for Transdermal Biosensing: Current Picture and Future Direction," Adv. Healthc. Mat., 4:2606-2640 (2015).
Vittal et al., "Surfactant Promoted Enhancement on Electrochemical and Electrochromic Properties of Film and Prussian Blue and Its Analogs," Journal of the Electrochemical Society, 146(2): 786-793 (1999).
Vo et al., "Strategies for controlled delivery of growth factors and cells for bone regeneration," Adv Drug Deliv Rev, 64(12): 1292-1309 (2012).

Volinia et al., "Breast cancer signatures for invasiveness and prognosis defined by deep sequencing of microRNA," Proc. Nat. Acad. Sci. USA, 109(8):3024-3029 (2012).
Vrdoljak et al., "Induction of broad immunity by thermostabilised vaccines incorporated in dissolvable microneedles using novel fabrication methods," J Control Release, 225:192-204 (2016).
Wang et al., "A Novel Biodegradable Gene Carrier Based on Polyphosphoester," J Am Chem Soc, 123: 9480-9481 (2001).
Wang et al., "Minimally Invasive Extraction of Dermal Interstitial Fluid for Glucose Monitoring Using Microneedles," Diabetes Technol. Ther., 7:131-141 (2005).
Wang et al., "Precise Microinjection into Skin Using Hollow Microneedles," J Invest Dermatol, 126:1080-1087 (2006).
Wang et al., "Synthesis and evaluation of water-soluble polymeric bone-targeted drug delivery systems," Bioconjugate Chemistry 14(5): 853-859 (2003).
Warner et al., "Nonsteroid Drug Selectives for Cyclo-Oxygenase-1 Rather Than Cyclo-Oxygenase-2 are Associated with Human Gastrointestinal Toxicity: A Full in vitro Analysis," Proc Natl Acad Sci USA, 96: 9966 (1999).
Watts et al., "Long-Term Use of Bisphosphonates in Osteoporosis," J Clin Endocr Metab, 95(4): 1555-1565 (2010).
Weber et al., "The MicroRNA Spectrum in 12 Body Fluids," Clin. Chem., 56(11): 1733-1741 (2010).
Wesbey et al., "Paramagnetic pharmaceuticals for magnetic resonance imaging," Physiological Chemistry and Physics and Medical NMR, 16(2): 145-155 (1984).
Wick et al., "Profound CD8+ T cell immunity elicited by sequential daily immunization with exogenous antigen plus the TLR3 agonist poly(I:C)," Vaccine 29: 984-993 (2011).
Wikipedia, Heparin, accessed Oct. 15, 2014, pp. 1-18.
Will et al., "Porous ceramic bone scaffolds for vascularized bone tissue regeneration," Journal of Materials Science, 19(8): 2781-2790 (2008).
Winer et al., "Optimizing Treatment of 'Triple-Negative,'" Breast Cancer. SABCS 2007: Improvising Outcomes in Advanced and Meta-static Breast Cancer (2007).
Woeblecke et al., "Reversal of Breast Cancer Resistance Protein-Mediated Drug Resistance by Tryoprostatin A," International Journal of Cancer, 107: 721-728 (2003).
Wolf., "Contrast enhancement in biomedical NMR", Physiological Chemistry and Physics and Medical NMR, 16(2): 93-95 (1984).
Wood et al., "A Unique Structure for Epidermal Growth Factor Receptor Bound to GW572016 (Lapatinib): Relationships Among Protein Conformation, Inhibitor Off-Rate, and Receptor Activity in Tumor Cells," Cancer Research, 64: 6652-6659 (2004).
Wood et al., "Controlling Interlayer Diffusion to Achieve Sustained, Multiagent Delivery from Layer-by-Layer Thin Films," Proc Natl Acad Sci USA, 103(27): 10207-10212 (2006).
Wood et al., "Tunable drug release from hydrolytically degradable layer-by-layer thin films," Langmuir, 21(4):1603-9 (2005).
Woodruff et al., "Bone tissue engineering: from bench to bedside," Materials Today, 15(10): 430-435 (2012).
Written Opinion for PCT/US06/04295, dated Oct. 2, 2006.
Written Opinion for PCT/US08/66948 dated Aug. 23, 2008.
Written Opinion for PCT/US11/35057, dated Feb. 8, 2012.
Written Opinion for PCT/US2002/34191 dated Jun. 17, 2003.
Written Opinion for PCT/US2014/018284, dated Jul. 30, 2014.
Written Opinion for PCT/US2014/022107, dated Jun. 5, 2014.
Written Opinion for PCTUS2007/69937 dated Aug. 13, 2008.
Written Opinion for PCTUS2007/69964 dated: Oct. 29, 2007.
Yang et al., "A New Approach to Identifying Genotoxic Carcinogens: p53 Induction as an Indicator of Genotoxic Damage," Carcinogenesis, 19:1117-1125 (1998).
Yoon et al., "Activation of p38 Mitogen-Activated Protein Kinase Is Required for Death Receptor-Independent Caspase-8 Activation and Cell Death in Response to Sphingosine," Molecular Cancer Research, 7(3): 361-370 (2009).
Zauner et al., "Polylysine-Based Transfection Systems Utilizing Receptor-Mediated Delivery," Adv Drug Del Rev, 30: 97-113 (1998).

(56) References Cited

OTHER PUBLICATIONS

Zhang et al., "In Vitro Observations of Self-Assembled ECM-Mimetic Bioceramic; Nanoreservoir Delivering rFN/CDH to Modulate Osteogenesis", Biomaterials, 33(30): 7468-7477 (2012).

Zhang et al., "Multilayered Thin Films that Sustain the Release of Functional DNA under Physiological Conditions," Langmuir, 20(19): 8015-8021 (2004).

Zhang et al., "Structure/property relationships in erodible multilayered films: influence of polycation structure on erosion profiles and the release of anionic polyelectrolytes," Langmuir, 22:239-245 (2006).

Zheng et al., "Controlling cell attachment selectively onto biological polymer-colloid templates using polymer-on-polymer stamping," Langmuir, 20(17):7215-22 (2004).

Zhou et al., "Preparation of Poly(L-serine ester): A Structural Analogue of Conventional Poly(L-serine)," Macromolecules, 23: 3399-3406 (1990).

\* cited by examiner

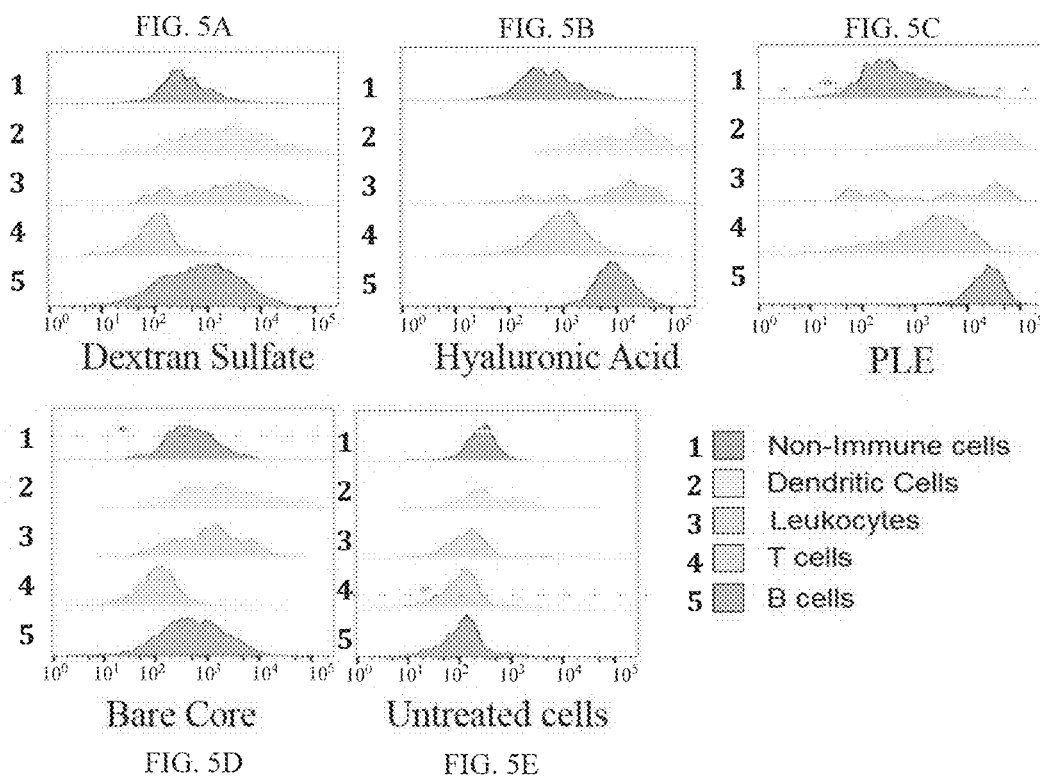

LAYER-BY-LAYER NANOPARTICLES FOR CYTOKINE THERAPY IN CANCER TREATMENT

RELATED APPLICATIONS

This application is a continuation of U.S. patent application Ser. No. 16/175,311, filed Oct. 30, 2018, which claims the benefit of priority to U.S. Patent Application Ser. No. 62/578,2730, filed Oct. 30, 2017, the contents of each of which are hereby incorporated by reference.

STATEMENT OF GOVERNMENT SUPPORT

This invention was made with Government support under Grant No. W81XWH-13-1-0151 awarded by the U.S. Army Medical Research and Material Command. The Government has certain rights in the invention.

BACKGROUND

Effective cancer treatment is a challenge due to the heterogeneity of cancer as a disease. The term "cancer" covers hundreds of malignancies that differ based on mutation history and tissue of origin. These differences can make targeting treatment very difficult.

Immunotherapy uses a patient's immune system to recognize and fight tumors. Immunotherapies come in a variety of forms, including monoclonal antibodies, cancer vaccines, checkpoint inhibitors, and general immune stimulants. Cytokines (such as IL-12), which are small signaling proteins used by the immune system to control immune responses, can be used as a general immune stimulant when delivered exogenously. This class of treatment refers to a drug that simply activates the immune system in the local environment where it is delivered.

However, cytokine therapies often result in high off-target toxicity. Thus, there is an unmet need for compositions and delivery methods for cytokines to reduce systemic side effects.

SUMMARY OF THE INVENTION

The present disclosure provides a particle for cytokine delivery useful in cancer treatment. Such particles may have properties advantageous in cancer immunotherapy, while reducing systemic side effects.

In some embodiments, the invention relates to a particle comprising a liposome, wherein the liposome comprises a first lipid covalently bonded to an affinity ligand; and the first lipid forms an outer surface of the liposome. In certain embodiments, the invention relates to a particle comprising a protein covalently bonded to a tag, wherein the tag is associated with the affinity ligand. In certain embodiments, the invention relates to a particle comprising a polymer coating, wherein the polymer coating comprises: at least one layer including a polycation, wherein the polycation is non-covalently associated with the outer surface of the liposome; and at least one layer including a polyanion, wherein the polyanion is non-covalently associated with at least one polycation layer.

In certain embodiments, the invention relates to a pharmaceutical formulation comprising a plurality of particles and a pharmaceutically acceptable carrier.

In certain embodiments, the invention relates to a method of treating cancer comprising administering to a subject in need thereof a therapeutically effective amount of a particle.

BRIEF DESCRIPTION OF THE DRAWINGS

FIG. 5A is a plot showing the efficiency with which particles coated with dextran sulfate target immune cells. Fluorescent core particles were coated with PLR followed by DXS and incubated in whole splenocyte culture for 18 hrs. Cultures were then measured for particle associated fluorescence by flow cytometry. Immune populations were gated by non-immune cells: CD45−, Dendritic Cells CD45+ CD11c+, Leukocytes CD45+ CD11b+, T cells: CD45+ CD3+, B cells CD45+ B220+. Data show histograms of cell number on the y-axis with median fluorescence intensity in the particle channel in the x-axis.

FIG. 5B is a plot showing the efficiency with which particles coated with hyaluronic acid target immune cells (similar to FIG. 5A).

FIG. 5C is a plot showing the efficiency with which particles coated with poly(L-glutamic acid) target immune cells (similar to FIG. 5A).

FIG. 5D is a plot showing the efficiency with which control particles target immune cells (similar to FIG. 5A).

FIG. 5E is a plot showing the efficiency with which uncoated particles target immune cells (similar to FIG. 5A).

FIG. 8A MC38 tumor volumes of individual mice treated intratumorally with PBS weekly beginning day 6 after tumor inoculation for 5 treatments.

FIG. 8B MC38 tumor volumes of individual mice treated intratumorally with control nanoparticles (no scIL-12 loading, PLE terminal particles) weekly beginning day 6 after tumor inoculation for 5 treatments.

FIG. 8C MC38 tumor volumes of individual mice treated intratumorally with 5 µg scIL-12 loaded Ni-HIS particles with PLE terminal layer weekly beginning day 6 after tumor inoculation for 5 treatments.

FIG. 8D MC38 tumor volumes of individual mice treated intratumorally with 5 µg soluble scIL-12 weekly beginning day 6 after tumor inoculation for 5 treatments.

FIG. 8E MC38 tumor volumes of individual mice treated intratumorally with 7.5 µg scIL-12 loaded Ni-HIS particles with PLE terminal layer weekly beginning day 6 after tumor inoculation for 5 treatments.

FIG. 8F MC38 tumor volumes of individual mice treated intratumorally with 5 µg scIL-12 loaded Ni-HIS particles with PLE terminal layer 2× weekly beginning day 6 after tumor inoculation for 5 treatments.

FIG. 8G Average tumor volumes on day 13 from FIGS. 8A-8F. Significance measured by one-way ANOVA with Bonferonni posttest. *** corresponds to p<0.001.

FIG. 8H Survival data of FIGS. 8A-8F. Significance measured by Log-rank tests.

FIG. 9A MC38 tumor volumes of individual mice bearing 2 tumors, with one tumor treated intratumorally with PBS weekly beginning day 6 after tumor inoculation for 5 treatments, treated tumors.

FIG. 9B MC38 tumor volumes of individual mice bearing 2 tumors, with one tumor treated intratumorally with 5 µg soluble scIL-12 weekly beginning day 6 after tumor inoculation for 5 treatments, treated tumors.

FIG. 9C MC38 tumor volumes of individual mice bearing 2 tumors, with one tumor treated intratumorally with 5 µg scIL-12 Ni-HIS particles with PLE terminal layer weekly beginning day 6 after tumor inoculation for 5 treatments, treated tumors.

FIG. 9D MC38 tumor volumes of individual mice bearing 2 tumors, with one tumor treated intratumorally with PBS weekly beginning day 6 after tumor inoculation for 5 treatments, untreated tumors.

FIG. 9E MC38 tumor volumes of individual mice bearing 2 tumors, with one tumor treated intratumorally with 5 µg soluble scIL-12 weekly beginning day 6 after tumor inoculation for 5 treatments, untreated tumors.

FIG. 9F MC38 tumor volumes of individual mice bearing 2 tumors, with one tumor treated intratumorally with 5 µg scIL-12 Ni-HIS particles with PLE terminal layer weekly beginning day 6 after tumor inoculation for 5 treatments, untreated tumors.

FIG. 9G Average tumor sizes on day 17 from FIGS. 9A-9C.

FIG. 9H Average tumor sizes on day 17 from FIGS. 9D-9F.

FIG. 9I Survival from FIG. 9A-9F.

FIG. 10A HM-1 tumor volumes of individual mice treated intratumorally with PBS weekly beginning day 6 after tumor inoculation for 5 treatments.

FIG. 10B HM-1 tumor volumes of individual mice treated intratumorally with control nanoparticles (no scIL-12 loading, PLE terminal particles) weekly beginning day 6 after tumor inoculation for 5 treatments.

FIG. 10C HM-1 tumor volumes of individual mice treated intratumorally with 5 µg scIL-12 loaded Ni-HIS particles with PLE terminal layer weekly beginning day 6 after tumor inoculation for 5 treatments.

FIG. 10D HM-1 tumor volumes of individual mice treated intratumorally with 5 µg soluble scIL-12 weekly beginning day 6 after tumor inoculation for 5 treatments.

FIG. 10E Average tumor volumes on day 24 from FIGS. 10A-10D. Significance measured by one-way ANOVA with Bonferonni post test. ** corresponds to p<0.01.

FIG. 10F Survival data of FIG. 10A-10D. Significance measured by Log-rank tests.

DETAILED DESCRIPTION OF THE INVENTION

Overview

Figure 1A:
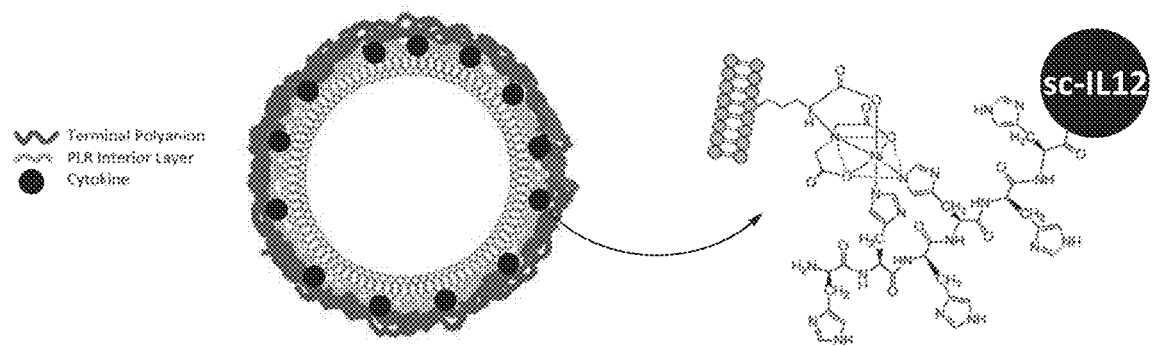
FIG. 1A is a schematic representation of different loading techniques for a liposomal core nanoparticle loaded with scIL-12.

In certain embodiments, the invention relates to developing delivery systems for proteins, such as cytokines, that exhibit improved safety profiles. For example, in certain embodiments, the invention relates to a single-chain version of IL-12 (scIL-12) in a layer-by-layer nanoparticle that packages the cytokine in a manner that avoids off-target toxicity while maintaining its bioactivity.

Loading proteins, such as IL-12 and similar cytokines, into particles can be a challenge because proteins are very susceptible to conformational changes brought about by heat, sonication, or pH changes, all of which are common in formulating particles for delivering active agents.

To maintain its therapeutic efficacy, the protein must be encapsulated in such a way that it is able to interact with an external receptor found on T and natural killer (NK) cells. This poses a challenge because particles are usually designed to be internalized, and these immune cells are relatively rare in the tumor environment. Therefore, in addition to designing the particles for drug release, in certain embodiments, the particles comprise different polymeric coating materials for targeting the particle to the tumor as a method of avoiding off target exposure.

In certain embodiments, layer-by-layer technology is used to tailor the delivery properties of the particle in order to maximize the efficacy of anticancer agent in the tumor while keeping its off-target toxicity in check. Layer-by-layer nanoparticles may be created by using electrostatic and metallic affinity interactions to coat a colloidal substrate with polymeric materials. The addition of layered materials allows for optimized targeting and delivery of the payload as well as the combination of different payloads within a single particle.

In certain embodiments, the invention relates to particles where the protein is effectively encapsulated. In certain embodiments, the invention relates to particles that exhibit activity on external receptors in a relatively rare cell population in a tumor. In certain embodiments, the invention relates to particles exhibiting reduced toxicity while maintaining efficacy against a tumor challenge.

Glossary

As used herein, the term "monomer," unless otherwise indicated, includes both isolated monomers and residues of monomers in an oligomer or a polymer (i.e. repeat units or residues).

The term "polyelectrolyte", as used herein, refers to a polymer which under a particular set of conditions (e.g., physiological conditions) has a net positive or negative charge. In some embodiments, a polyelectrolyte is or comprises a polycation; in some embodiments, a polyelectrolyte is or comprises a polyanion. Polycations have a net positive charge and polyanions have a net negative charge. The net charge of a given polyelectrolyte may depend on the surrounding chemical conditions, e.g., on the pH. Exemplary polyelectrolytes for use in polymeric coatings in the compositions of the invention include, but are not limited to: poly(L-arginine) (PLR), poly-L-glutamic acid (PLE), polyarginine, polyglutamic acid, polylysine, heparin folate, heparin sulfate, fucoidan, sulfated-β-cyclodextrin, hyaluronic acid (HA), polyglutamic acid-block-polyethylene glycol, polyaspartic acid, polystyrene sulfonate (SPS), polyacrylic acid (PAA), linear poly(ethylene imine) (LPEI), poly(diallyldimethyl ammonium chloride) (PDAC), polyallylamine hydrochloride (PAH), poly(L-lactide-co-L-lysine), polyserine ester, poly(4-hydroxy-L-proline ester), poly[α-(4-aminobutyl)-L-glycolic acid], sodium polystyrene sulfonate, dextran sulfate (DXS), alginate, and chondroitin sulfate.

In certain embodiments, linkers (also known as "linker molecules" or "cross-linkers" or "spacers") may be used to conjugate one atom to another in a composition. The majority of known linkers react with amine, carboxyl, and sulfhydryl groups. Linker molecules may be responsible for different properties of the composition. The length of the linker should be considered in light of molecular flexibility during the conjugation step, and the availability of the conjugated molecule for its target. Longer linkers may thus improve the biological activity of the compositions of the invention, as well as the ease of preparation of them. The geometry of the linker may be used to orient a molecule for optimal reaction with a target. A linker with flexible geometry may allow the entire composition to conformationally adapt as it binds a target sequence. The nature of the linker may be altered for other various purposes. For example, the hydrophobicity of a polymeric linker may be controlled by the order of monomeric units along the polymer, e.g. a block polymer in which there is a block of hydrophobic monomers interspersed with a block of hydrophilic monomers.

The chemistry of preparing and utilizing a wide variety of molecular linkers is well-known in the art and many premade linkers for use in conjugating molecules are commercially available from vendors such as Pierce Chemical Co., Roche Molecular Biochemicals, United States Biological. Exemplary linker molecules for use in the compositions of the invention include, but are not limited to: aminocaproic acid (ACA); polyglycine, and any other amino acid polymer, polymers such as polyethylene glycol (PEG), polymethyl methacrylate (PMMA), polypropylene glycol (PPG); homobifunctional reagents such as APG, AEDP, BASED, BMB, BMDB, BMH, BMOE, BM[PEO]3, BM[PEO]4, BS3, BSOCOES, DFDNB, DMA, DMP, DMS, DPDPB, DSG, DSP (Lomant's Reagent), DSS, DST, DTBP, DTME, DTSSP, EGS, HBVS, Sulfo-BSOCOES, Sulfo-DST, Sulfo-EGS; heterobifunctional reagents such as ABH, AEDP, AMAS, ANB-NOS, APDP, ASBA, BMPA, BMPH, BMPS, EDC, EMCA, EMCH, EMCS, KMUA, KMUH, GMBS, LC-SMCC, LC-SPDP, MBS, MBuS, M2C2H, MPBH, MSA, NHS-ASA, PDPH, PMPI, SADP, SAED. SAND, SANPAH, SASD, SATP, SBAP, SFAD, SIA, SIAB, SMCC, SMPB, SMPH, SMPT, SPDP, Sulfo-EMCS, Sulfo-GMBS, Sulfo-HSAB, Sulfo-KMUS, Sulfo-LC-SPDP, Sulfo-MBS. Sulfo-NHS-LC-ASA, Sulfo-SADP, Sulfo-SANPAH, Sulfo-SIAB, Sulfo-SMCC, Sulfo-SMPB, Sulfo-LC-SMPT, SVSB, TFCS; and trifunctional linkers such as Sulfo-SBED.

Branched linkers may be prepared or used so that multiple moieties per linker are able to react. Such multiply reactive linkers allow the creation of multimeric binding sites.

The term "pKa," as used herein, includes the negative decadic logarithm of the ionization constant (Ka) of an acid; equal to the pH value at which equal concentrations of the acid and conjugate base forms of a substance (often a buffer) are present.

The term "hydrophobic," as used herein, refers to a compound that has an octanol/water partition coefficient (Kow) greater than about 10 at about 23° C.

The term "hydrophilic," as used herein, refers to a compound that has an octanol/water partition coefficient (Kow) less than about 10 at about 23° C.

As used herein, the term "pharmaceutically acceptable carrier" refers to a pharmaceutically-acceptable material, composition or vehicle for administration of an active agent described herein. Pharmaceutically acceptable carriers include any and all solvents, dispersion media, coatings, antibacterial and antifungal agents, isotonic and absorption delaying agents, and the like which are compatible with the activity of the active agent and are physiologically acceptable to the subject. Some examples of materials which can serve as pharmaceutically-acceptable carriers include: (i) sugars, such as lactose, glucose and sucrose; (ii) starches, such as corn starch and potato starch; (iii) cellulose, and its derivatives, such as sodium carboxymethyl cellulose, methylcellulose, ethyl cellulose, microcrystalline cellulose and cellulose acetate; (iv) powdered tragacanth; (v) malt; (vi) gelatin; (vii) lubricating agents, such as magnesium stearate, sodium lauryl sulfate and talc; (viii) excipients, such as cocoa butter and suppository waxes; (ix) oils, such as peanut oil, cottonseed oil, safflower oil, sesame oil, olive oil, corn oil and soybean oil; (x) glycols, such as propylene glycol; (xi) polyols, such as glycerin, sorbitol, mannitol and polyethylene glycol (PEG); (xii) esters, such as ethyl oleate and ethyl laurate; (xiii) agar; (xiv) buffering agents, such as magnesium hydroxide and aluminum hydroxide; (xv) alginic acid; (xvi) pyrogen-free water; (xvii) isotonic saline; (xviii) Ringer's solution; (xix) ethyl alcohol; (xx) pH buffered solutions; (xxi) polyesters, polycarbonates and/or polyanhydrides; (xxii) bulking agents, such as polypeptides and amino acids (xxiii) serum component, such as serum albumin, HDL and LDL; (xxiv) C2-C12 alcohols, such as ethanol; and (xxv) other non-toxic compatible substances employed in pharmaceutical formulations. Wetting agents, coloring agents, release agents, coating agents, sweetening agents, flavoring agents, perfuming agents, preservative and antioxidants can also be present in the formulation. For formulations described herein to be administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Pharmaceutically acceptable carriers can vary in a formulation described herein, depending on the administration route. The formulations described herein can be delivered via any administration mode known to a skilled practitioner. For example, the formulations described herein can be delivered in a systemic manner, via administration routes such as, but not limited to, oral, and parenteral, including intravenous, intramuscular, intraperitoneal, intradermal, and subcutaneous. In some embodiments, the formulations described herein are in a form that is suitable for injection. In other embodiments, the formulations described herein are formulated for oral administration.

When administering parenterally, a formulation described herein can be generally formulated in a unit dosage injectable form (solution, suspension, emulsion). The formulations suitable for injection include sterile aqueous solutions or dispersions. The carrier can be a solvent or dispersing medium containing, for example, water, cell culture medium, buffers (e.g., phosphate buffered saline), polyol (for example, glycerol, propylene glycol, liquid polyethylene glycol, and the like), suitable mixtures thereof. In some embodiments, the pharmaceutical carrier can be a buffered solution (e.g., PBS). Where necessary, the composition may also include a solubilizing agent and a local anesthetic such as lignocaine to ease pain at the site of the injection.

The formulations can also contain auxiliary substances such as wetting or emulsifying agents, pH buffering agents, gelling or viscosity enhancing additives, preservatives, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation. With respect to formulations described herein, however, any vehicle, diluent, or additive used should have to be biocompatible with the active agents described herein. Those skilled in the art will recognize that the components of the formulations should be selected to be biocompatible with respect to the active agent. This will present no problem to those skilled in chemical and pharmaceutical principles, or problems can be readily avoided by reference to standard texts or by simple experiments (not involving undue experimentation).

For in vivo administration, the formulations described herein can be administered with a delivery device, e.g., a syringe. Accordingly, an additional aspect described herein provides for delivery devices comprising at least one chamber with an outlet, wherein the at least one chamber comprises a pre-determined amount of any formulation described herein and the outlet provides an exit for the formulation enclosed inside the chamber. In some embodiments, a delivery device described herein can further comprise an actuator to control release of the formulation through the outlet. Such delivery device can be any device to facilitate the administration of any formulation described herein to a subject, e.g., a syringe, a dry powder injector, a nasal spray, a nebulizer, or an implant such as a microchip, e.g., for sustained-release or controlled release of any formulation described herein.

The nomenclature used to define the peptides is that typically used in the art wherein the amino group at the N-terminus appears to the left and the carboxyl group at the C-terminus appears to the right.

As used herein, the term "amino acid" includes both a naturally occurring amino acid and a non-natural amino acid. The term "amino acid," unless otherwise indicated, includes both isolated amino acid molecules (i.e. molecules that include both, an amino-attached hydrogen and a carbonyl carbon-attached hydroxyl) and residues of amino acids (i.e. molecules in which either one or both an amino-attached hydrogen or a carbonyl carbon-attached hydroxyl are removed). The amino group can be alpha-amino group, beta-amino group, etc. For example, the term "amino acid alanine" can refer either to an isolated alanine H-Ala-OH or to any one of the alanine residues H-Ala-, -Ala-OH, or -Ala-. Unless otherwise indicated, all amino acids found in the compounds described herein can be either in D or L configuration. The term "amino acid" includes salts thereof, including pharmaceutically acceptable salts. Any amino acid can be protected or unprotected. Protecting groups can be attached to an amino group (for example alpha-amino group), the backbone carboxyl group, or any functionality of the side chain. As an example, phenylalanine protected by a benzyloxycarbonyl group (Z) on the alpha-amino group would be represented as Z-Phe-OH.

A protected amino acid is an amino acid in which one or more functional groups are protected with a protecting group. A protected peptide fragment is a dipeptide, tripeptide, or tetrapeptide, in which one or more functional groups of the amino acid of the peptide fragment are protected with a protecting group. Preferably, the protected amino acid and/or protected peptide fragment of the present invention have a protected amino group. The term "amino protecting group" refers to protecting groups which can be used to replace an acidic proton of an amino group in order to reduce its nucleophilicity.

Examples of amino protecting groups (e.g. X1, X2, X3, X4, etc.) include but are not limited to substituted or unsubstituted groups of acyl type, such as the formyl, acrylyl (Acr), benzoyl (Bz), acetyl (Ac), trifluoroacetyl, substituted or unsubstituted groups of aralkyloxycarbonyl type, such as the benzyloxycarbonyl (Z), p-chlorobenzyloxycarbonyl, p-bromobenzyloxycarbonyl, p-nitrobenzyloxycarbonyl, p-methoxybenzyloxycarbonyl, benzhydryloxycarbonyl, 2(p-biphenylyl)isopropyloxycarbonyl, 2-(3,5-dimethoxyphenyl)isopropyloxycarbonyl, p-phenylazobenzyloxycarbonyl, triphenylphosphonoethyloxycarbonyl or 9-fluorenylmethyloxycarbonyl group (Fmoc), substituted or unsubstituted groups of alkyloxycarbonyl type, such as the tert-butyloxycarbonyl (BOC), tert-amyloxycarbonyl, diisopropylmethyloxycarbonyl, isopropyloxycarbonyl, ethyloxycarbonyl, allyloxycarbonyl, 2 methylsulphonylethyloxycarbonyl or 2,2,2-trichloroethyloxycarbonyl group, groups of cycloalkyloxycarbonyl type, such as the cyclopentyloxycarbonyl, cyclohexyloxycarbonyl, adamantyloxycarbonyl or isobornyloxycarbonyl group, and groups containing a hetero atom, such as the benzenesulphonyl, p-toluenesulphonyl, mesitylenesulphonyl, methoxytrimethylphenylsulphonyl, 2-nitrobenzenesulfonyl, 2-nitrobenzenesulfenyl, 4-nitrobenzenesulfonyl or 4-nitrobenzenesulfenyl group. Among these groups X, those comprising a carbonyl, a sulfenyl or a sulphonyl group are preferred. An amino protecting groups X1, X2, X3, X4, etc. is preferably selected from allyloxycarbonyl groups, tert-butyloxycarbonyl (BOC), benzyloxycarbonyl (Z), 9 fluorenylmethyloxycarbonyl (Fmoc), 4-nitrobenzenesulfonyl (Nosyl), 2-nitrobenzenesulfenyl (Nps) and substituted derivatives.

Preferred amino protecting groups X1, X2, X3, X4, etc. for the process of the present invention are tert-butyloxycarbonyl (Boc), a 9-fluorenylmethyloxycarbonyl (Fmoc), and a benzyloxy-carbonyl (Z). Even more preferred amino protecting groups for the process of the present invention are tert-butyloxycarbonyl (Boc) and a benzyloxy-carbonyl (Z).

Amino protecting groups X1, X2, X3, X4, etc. can be introduced by various methods as known in the art. For example, by reaction with suitable acid halides or acid anhydrides. On the other hand, amino protecting groups X1, X2, X3, X4, etc. can be removed (i.e., the step of deprotecting), for example, by acidolysis, hydrogenolysis (e.g., in the presence of hydrogen (e.g. bubbled through the liquid reaction medium) and catalyst such as palladium catalyst), treatment with dilute ammonium hydroxide, treatment with hydrazine, treatment with sodium and treatment with sodium amide.

As used herein, the term "tag" refers to a compound, for example a peptide, that can be used for purification, for solubilization, chromatography, as epitope tags, fluorescence tags, and others. Tags useful in the present invention include, but are not limited to, BCCP, c-myc-tag, Calmodulin-tag, FLAG-tag, HA-tag, His-tag, Maltose binding protein-tag, Nus-tag, Glutathione-S-transferase (GST) tag, Green fluorescent protein-tag, Thioredoxin-tag, S-tag, Streptag II, Softag 1, Softag 3, T7-tag, Elastin-like peptides, Chitin-binding domain, and Xylanase 10A.

As used herein, the term "affinity" refers to the equilibrium constant for the reversible binding of two agents (e.g., tag and a ligand, or a metal ion and a ligand) and is expressed as a dissociation constant (KD). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1,000-fold greater, or more, than the affinity of a ligand for unrelated peptides or compounds. Affinity of a ligand to its binding partner can be, for example, from about 100 nanomolar (nM) to about 0.1 nM, from about 100 nM to about 1 picomolar (pM), or from about 100 nM to about 1 femtomolar (fM) or more. An "affinity ligand" is a ligand having affinity for a binding partner.

As used herein, the term "associated with" refers to a direct association between two molecules, due to, for example, covalent, electrostatic, hydrophobic, and ionic and/or hydrogen-bond interactions.

As used herein, the term "coordinated with" refers to, in coordination chemistry, the association between a metal atom or metal ion and an ion or molecule (e.g., a functional group on a ligand). The binding between metal and ligand generally involves formal donation of one or more of the ligand's electron pairs. The nature of the metal-ligand bonding can range from covalent to ionic.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. An example of a protein is an antibody.

As used herein, the term "peptide fragment" refers to two or more amino acids covalently linked by at least one amide bond (i.e. a bond between an amino group of one amino acid and a carboxyl group of another amino acid selected from the amino acids of the peptide fragment). The terms "polypeptide" and "peptide fragments" are used interchangeably. The term "peptide fragment" includes salts thereof, including pharmaceutically acceptable salts.

A cytokine is a signaling protein regulating biological functions such as innate and acquired immunity, hematopoiesis, inflammation and repair, and proliferation through mostly extracellular signaling.

Interleukin 12 (Il-12 or IL-12) is a cytokine that is naturally produced by dendritic cells, macrophages, neutrophils, and human B-lymphoblastoid cells in response to antigenic stimulation. Il-12 is composed of a bundle of four alpha helices. It is a heterodimeric cytokine encoded by two separate genes, Il-12A (p35) and Il-12B (p40).

Single chain interleukin 12 (scIl-12) is a protein in which the p35 and p40 subunits of heterodimeric IL-12 are covalently bonded together. For example, interleukin 12 can be monomerized by introduction of a peptide linker between the p35 and p40 protein chains of the heterodimeric cytokine. scIL-12 may be a fusion protein.

In certain embodiments, the invention relates to a particle comprising a liposome. In certain embodiments the liposome comprises a first lipid covalently bonded to an affinity ligand. In certain embodiments the first lipid forms an outer surface of the liposome. In certain embodiments, the invention relates to a particle comprising a protein covalently bonded to a tag. In certain embodiments the tag is associated with the affinity ligand. In certain embodiments, the invention relates to a particle comprising a polymer coating. In certain embodiments, the invention relates to a particle comprising the polymer coating comprising at least one layer including a polycation. In certain embodiments the polycation is non-covalently associated with the outer surface of the liposome. In certain embodiments, the invention relates to a particle comprising at least one layer including a polyanion. In certain embodiments the polyanion is non-covalently associated with the at least one polycation layer.

In certain embodiments, the invention relates to a particle comprising a metal ion. In certain embodiments, the invention relates to a particle comprising an affinity ligand which is a metal-affinity ligand. In certain embodiments, the invention relates to a particle comprising a tag which is a peptide tag. In certain embodiments, the invention relates to a particle comprising a metal ion that is coordinated with the metal-affinity ligand, thereby forming a metal-coordinated ligand. In certain embodiments, the invention relates to a particle comprising the peptide tag which is associated with the metal-coordinated ligand.

In certain embodiments, the invention relates to a particle comprising the affinity ligand which is non-covalently associated with the tag.

In certain embodiments, the invention relates to a particle comprising the affinity ligand which is covalently associated with the tag.

In certain embodiments, the invention relates to a particle comprising the metal-coordinated ligand which is non-covalently associated with the peptide tag.

In certain embodiments, the invention relates to a particle comprising the metal-affinity ligand which is iminodiacetic acid or iminodipropionic acid.

In certain embodiments, the invention relates to a particle comprising the metal ion selected from the group consisting of Fe(III), Co(II), Ni(II), Cu(II), and Zn(II).

In certain embodiments, the invention relates to a particle comprising the metal ion that is Ni(II).

In certain embodiments, the invention relates to a particle comprising the peptide tag which is at least two amino acid monomers in length.

In certain embodiments, the invention relates to a particle comprising the peptide tag which is at least three amino acid monomers in length.

In certain embodiments, the invention relates to a particle comprising the peptide tag which comprises a histidine monomer.

In certain embodiments, the invention relates to a particle comprising the peptide tag which comprises at least two histidine monomers.

In certain embodiments, the invention relates to a particle comprising the peptide tag which is a His6 tag.

In certain embodiments, the invention relates to a particle comprising the peptide tag which is covalently bonded to the C-terminus of the protein.

In certain embodiments, the invention relates to a particle comprising the first lipid which is 1,2-dioleoyl-sn-glycero-3-[(N-(5-amino-1-carboxypentyl)iminodiacetic acid)succinyl].

In certain embodiments, the invention relates to a particle comprising a second lipid; and the second lipid is a phosphatidylcholine.

In certain embodiments, the invention relates to a particle comprising the second lipid which is 1,2-distearoyl-sn-glycero-3-phosphocholine (DSPC).

In certain embodiments, the invention relates to a particle comprising a third lipid.

In certain embodiments, the invention relates to a particle comprising a third lipid which is 1-palmitoyl-2-oleoyl-sn-glycero-3-phospho-(1'-rac-glycerol) (POPG).

In certain embodiments, the invention relates to a particle comprising a fourth lipid; and the fourth lipid is cholesterol.

In certain embodiments, the invention relates to a particle comprising a protein which is non-covalently associated with the affinity ligand on the outer surface of the liposome.

In certain embodiments, the invention relates to a particle comprising a protein; and the protein is a cytokine.

In certain embodiments, the invention relates to a particle comprising a cytokine; and the cytokine is an interleukin or an interferon, or a single-chain variant of an interleukin or an interferon.

In certain embodiments, the invention relates to a particle comprising a cytokine; and the cytokine is an interleukin or a single-chain variant of an interleukin.

In certain embodiments, the invention relates to a particle comprising a cytokine; and the cytokine is IL-12 or a single-chain variant of IL-12.

In certain embodiments, the invention relates to a particle comprising a cytokine; and the cytokine is a single-chain variant of IL-12.

In certain embodiments, the invention relates to a particle comprising polycation selected from the group consisting of polyarginine and polylysine.

In certain embodiments, the invention relates to a particle comprising polycation; and the polycation is polyarginine.

In certain embodiments, the invention relates to a particle comprising polycation; and the polycation is poly-l-arginine.

In certain embodiments, the invention relates to a particle comprising polyanion selected from Heparin Folate, Heparin Sulfate, Dextran Sulfate, Fucoidan, Sulfated-B-cyclodextrin, Hyaluronic acid, Polyglutamic acid, Polyglutamic acid-block-polyethylene glycol, Polyaspartic acid, and Poly acrylic acid.

In certain embodiments, the invention relates to a particle comprising polyanion selected from polyglutamic acid and hyaluronic acid.

In certain embodiments, the invention relates to a particle comprising polyanion selected from poly-l-glutamic acid and hyaluronic acid.

In certain embodiments, the invention relates to a particle comprising a second polycation coating non-covalently associated with the outer surface of the polyanion coating; and a second polyanion coating non-covalently associated with the outer surface of the second polycation coating.

In certain embodiments, the invention relates to a pharmaceutical formulation comprising a plurality of particles and a pharmaceutically acceptable carrier.

In certain embodiments, the invention relates to a method of treating cancer comprising administering to a subject in need thereof a therapeutically effective amount of a particle.

In certain embodiments, the invention relates to a method of treating cancer, wherein the subject is human.

In certain embodiments, the invention relates to a method of treating cancer wherein the composition is administered intravenously.

EXEMPLIFICATION

The invention now being generally described, it will be more readily understood by reference to the following, which is included merely for purposes of illustration of certain aspects and embodiments of the present invention, and is not intended to limit the invention.

Example 1—Formation of Coated Liposomes

Figure 1B:
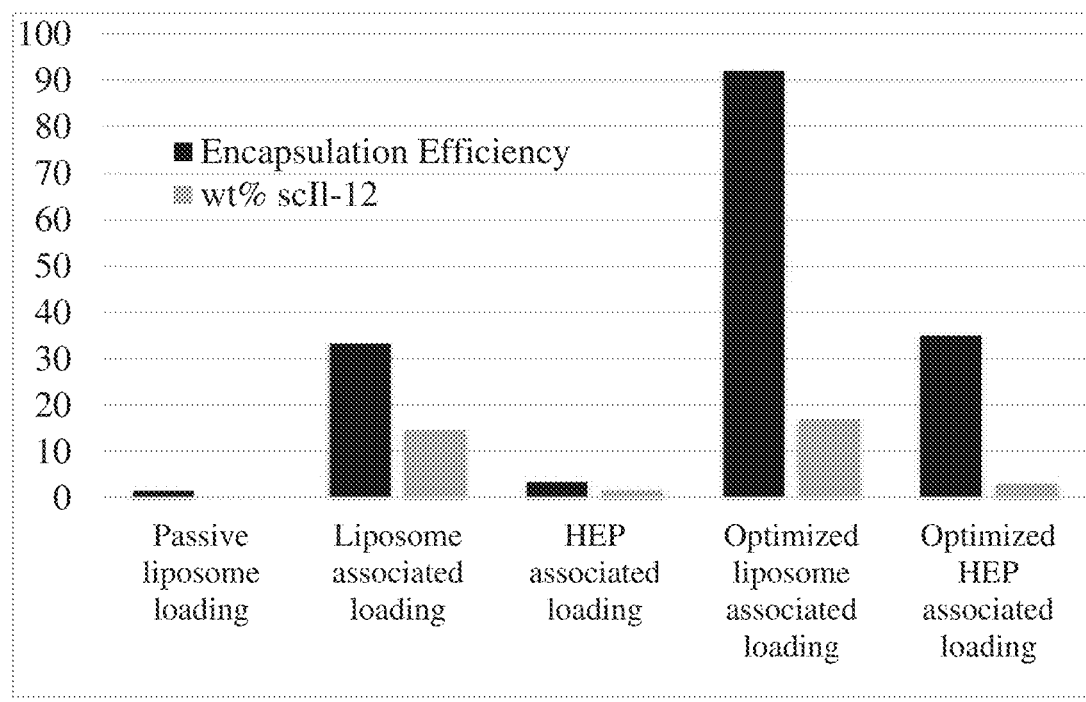
FIG. 1B is a bar graph showing encapsulation efficiency (left bar, measured as percent of initial IL-12 loaded in final particle) and weight % loading of cytokine (right bar) for different loading techniques in final layered particles. Optimized HEP and Optimized Ni refer to optimization of layering and purification techniques. Ni-HIS associated loading offers the highest encapsulation and wt % loading of cytokine by incorporation through attachment of the cytokine HIS tag to a Ni chelated on lipid head group.
Figure 4:
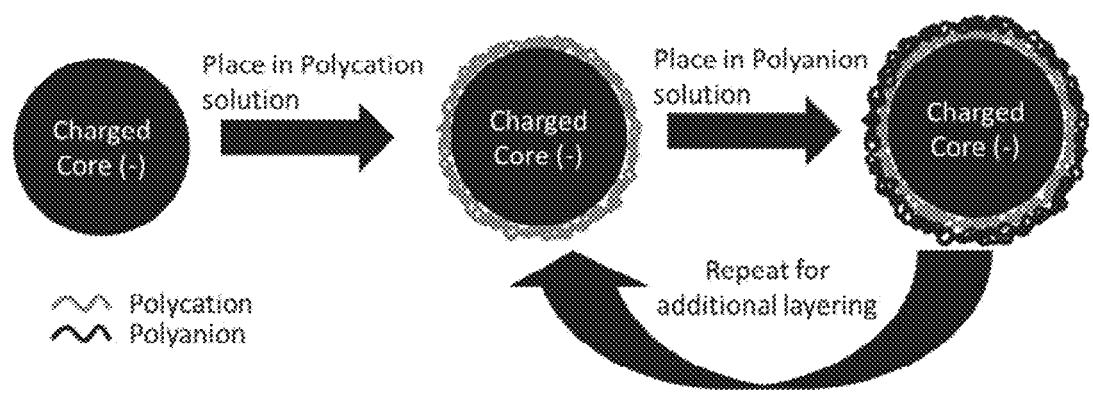
FIG. 4 is a schematic representation of layer-by-layer coating of particles.

A liposomal core nanoparticle with 5% DGS-NTA (Ni) (1,2-dioleoyl-sn-glycero-3-[(N-(5-amino-1-carboxypentyl) iminodiacetic acid)succinyl] nickel salt) lipid by mole was reacted with an scIL-12 construct which contains a 6×HIS tag at the c-terminus. This resulted in layering of the scIL-12 around the preformed liposome by Ni-HIS interaction. The scIL-12 liposome (which bears a negative charge) was then coated with a bilayer of poly(L-arginine) (PLR) and a terminal layer of polyanion using electrostatic interactions. The process of layer-by-layer particle formation is outlined in FIG. 4, and the resulting scIL-12-containing particles are depicted in FIG. 1A. The addition of these layers allowed for increased targeting of the particle to the tumor and reduction in systemic scIL-12 exposure. The optimization of this particle manufacturing procedure allowed for >90% encapsulation of protein with a final weight percentage of 17% scIL-12 in the particle, a large improvement over other techniques such as passive loading in the liposome or cytokine-heparin interaction in the layers FIG. 1B. The structure of layered liposomes was confirmed by CryoEM imaging of particle solutions, showing well-formed liposomes with polymer layers, of monodisperse size approximately 80-150 nm.

Example 2—Polymer Coating

A library of different external layer materials was tested for their tumor targeting and immune cell targeting capabilities to make the most effective delivery vehicle for scIL-12. A series of charged polypeptides have been studied as the external layers of nanoparticles, and have been shown to undergo differing amounts of binding versus internalization with different cell types. Flow cytometry was used to asses binding of particles to different cell types. Briefly, fluorescent core particles were coated with PLR followed by different polyanion terminal layers and incubated with different cell lines both cancerous and noncancerous for 24 hours. Cultures were then measured for particle associated fluorescence by flow cytometry. Hyaluronic acid and PLE terminal layers showed increased association with cancer cells as compared to noncancerous cell lines as measured by mean fluorescence intensity. Particles were measured for their association with immune populations by incubation with whole splenocytes for 18 hours. Immune populations were gated by non-immune cells: CD45−, Dendritic Cells CD45+ CDllc+, Leukocytes CD45+ CDllb+, T cells: CD45+ CD3+, B cells CD45+ B220+. Data show histograms of cell number on the y-axis with median fluorescence intensity in the particle channel in the x-axis (FIGS. 5A-5E). The data presented in FIGS. 5A-5E suggest these differences are based on specific interactions with proteins and glycans on the surfaces of cells of interest. These studies showed that hyaluronic acid (HA) and poly(L-glutamic acid) (PLE) have the highest association with cancer cells and relevant immune cells. Particles were further tested for subcellular localization via fluorescent microscopy. Fluorescent core particles were incubated for 6 or 24 hours on MC38 cancer cells. Cells were stained using wheat germ agglutinin to show the cell membrane and Hoechst to show the nucleus. These studies showed that PLE coated particles maintained greater degrees of extracellular, membrane bound association, while HA coated particles showed greater degrees of internalization.

Figure 2A:
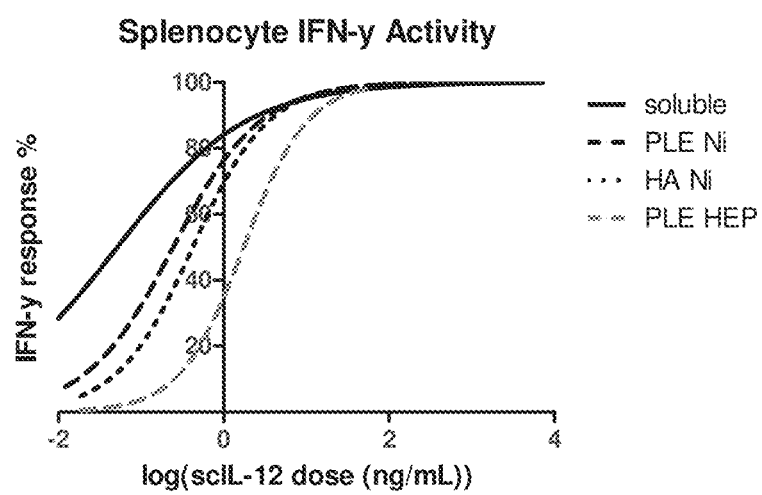
FIG. 2A is a plot showing IFN-γ responses as measured by ELISA to different scIL-12 formulations after incubation with whole isolated splenocytes for 18 hours.
Figure 2B:
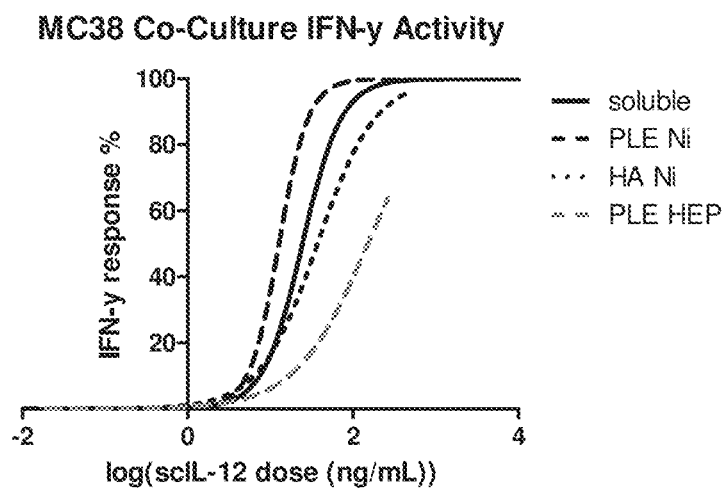
FIG. 2B is a plot showing co-culture activity of scIL-12 formulations in MC38 tumor mimic (Briefly, scIL-12 formulations were incubated with MC38 tumor cells for 6 hrs, cells were washed with PBS, whole splenocytes were added for 18 hrs, IFN-γ levels were measured with ELISA.
Figure 2C:
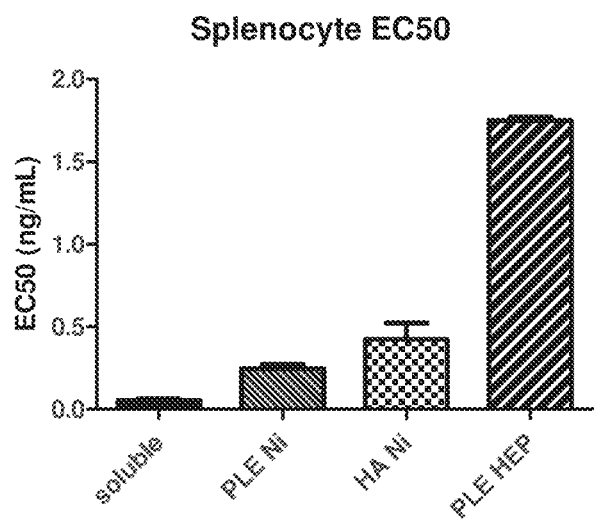
FIG. 2C is a bar graph showing the quantification of EC50 calculated from FIG. 2A.

Particles were formulated with both HA and PLE as the terminal layer, using either Ni-HIS loading or Heparin associated loading as described. These particles were tested in vitro for their ability to produce IFN-γ (a functional assay for IL-12 bioactivity) when incubated with primary murine splenocytes (FIGS. 2A, 2C). Splenocytes isolated from C57BL/6 mice were treated for 18 h with various formulations of scIL-12. Supernatants were measured with ELISA for IFN-γ production. Calculated EC50 values from nonlinear least squares fit with automatic outlier elimination in Prism 5 on log transformed, normalized data. Statistical significance calculated using 1-way ANOVA with Bonferroni post test (*** p<0.001). The IFN-γ responses and EC50 are shown in FIGS. 2A and 2C.

An additional in vivo mimic model was used, in which the particles are delivered to cancer cells, washed with PBS, and then primary murine splenocytes added to the treated cancer cells to ensure the particles maintained activity even after interaction with tumor cells which are much more prominent in the tumor microenvironment compared to target immune populations.

Sub-confluent tumor cells were treated with scIL-12 particles or control for 6 hours. Plates were washed with PBS and splenocyte cultures were added to wells for 18 hours. Supernatants were measured with ELISA for IFN-γ production. MC38 model statistical significance calculated using 1-way ANOVA with Bonferroni post test (*** p<0.001). The IFN-γ responses and EC50 are shown in FIGS. 2B and 2D.

Figure 2D:
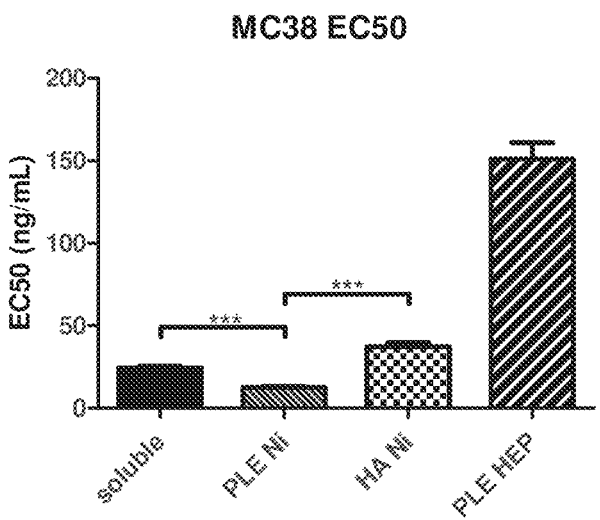
FIG. 2D is a bar graph showing the quantification of EC50 calculated from FIG. 2B. Only treatments that have shown tumor cell association in the past (HA, PLE terminal particles) maintained activity in the co-culture, while untargeted therapies (soluble scIL-12) showed much larger reduction in activity in co-culture. (*** indicates p<0.001 using one-way ANOVA with Bonferroni post test).
Figure 2E:
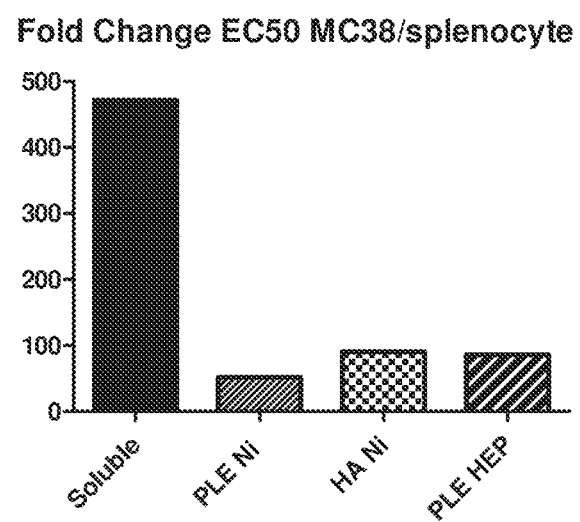
FIG. 2E shows fold change of MC38 co-culture experiment EC50 (FIG. 2D) over that of the splenocyte only culture (FIG. 2C).

As an additional measure of particle benefit over soluble therapy, the results shown in FIGS. 2C and 2D were combined as a measure of the maintenance of scIL-12 activity in the tumor environment. These results are shown in FIG. 2E as the fold change of MC38 co-culture EC50/Splenocyte only EC50.

These assays show that the nanoparticle formulations, particularly the Ni-HIS nanoparticles with PLE terminal layer, show enhanced activity over soluble scIL-12, with the PLE terminal layer performing best, particular in the tumor mimic co-culture environment and maintenance of activity.

Example 3—Toxicity

Figure 3:
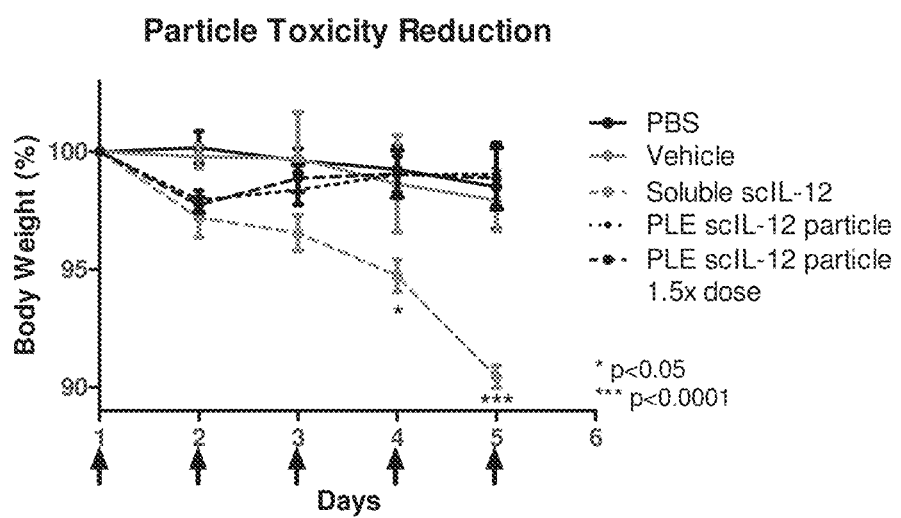
FIG. 3 is a plot of starting weight (%) versus time, which is used as a measure of particle toxicity. Mice were treated with 5 μg/mouse/day over 5 days of PLE terminal layer Ni-HIS associated scIL-12 particles (n=5) monitoring their weight daily at the time of injection. This treatment was compared to PBS injections of equal volume, particles without scIL-12 at equivalent dosing, soluble scIL-12 at equivalent dosing, and 1.5× dosing of particle bound scIL-12 (all n=3). Both particle doses showed significantly lower toxicity than the soluble cytokine, which reached 10% weight loss by day 5. Samples were compared using two-way ANOVA with Bonferroni post test.

A toxicity study was performed, delivering either 5 or 7.5 μg/mouse/day of scIL-12 in the Ni-HIS particles with PLE terminal layer over 5 days. Controls included 5 μg/mouse/day of soluble scIL-12 over the same period, particles without cytokine at equivalent dosing, and PBS. The mice were tracked for weight loss over the 5-day study period. The particle bound IL-12 showed a significant reduction in toxicity, losing negligible weight even at higher dosing compared to soluble IL-12 which saw approximately 10% reduction in body weight over 5 days FIG. 3.

Figure 6A:
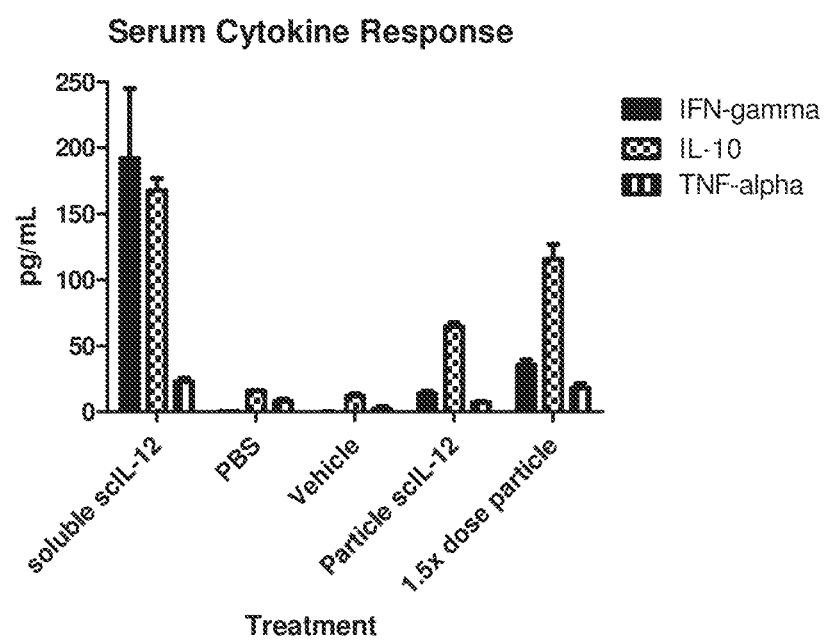
FIG. 6A is a bar graph showing serum cytokine responses (pg/mL) after various treatments. Serum was collected 3 hours after the final dose from FIG. 3.
Figure 6B:
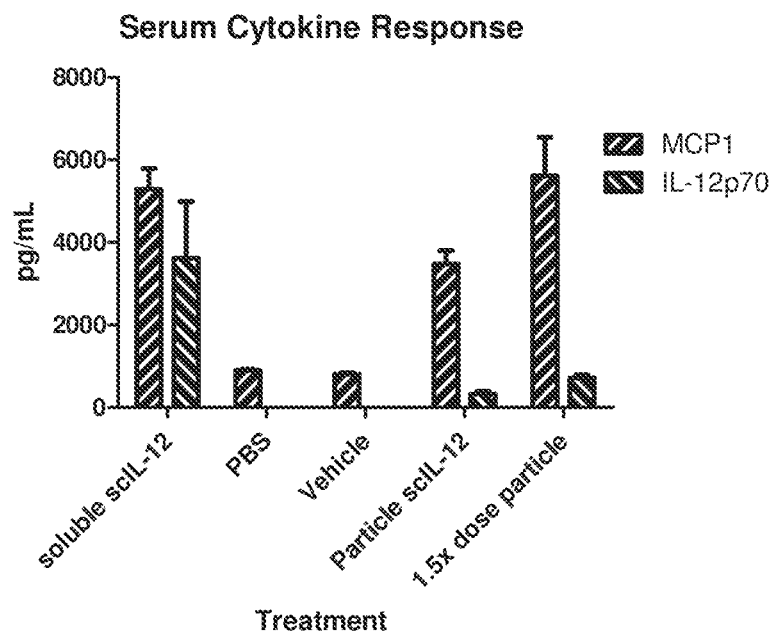
FIG. 6B is a bar graph showing serum cytokine responses (pg/mL) after various treatments. Serum was collected 3 hours after the final dose from FIG. 3.

At the end of the 5-day period serum was collected from the different groups and measured for inflammatory cytokine levels. Cytokine storm (as evidenced by elevated levels of inflammatory cytokines in circulation) is the route by which IL-12 therapy shows toxicity. FIGS. 6A and 6B show serum cytokine response depending on the scIL-12 formulation. These data agree with the weight changes, showing that particle bound scIL-12, even at higher dosing levels, is less toxic than its soluble counterpart.

Example 4—Tumor Challenge

Particle formulations were tested against a tumor challenge. MC38 and HM1 tumors grown subcutaneously were used.

Figure 7:
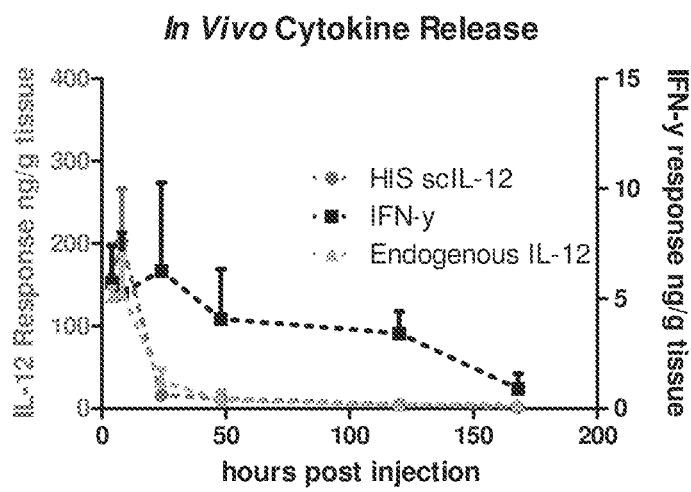
FIG. 7 is a graph showing temporal response of IFN-γ, delivered exogenous HIS-tagged scIL-12, and endogenously produced IL-12 in MC38 tumors after intratumoral treatment with 5 µg Ni-HIS particles with PLE terminal layer.

MC38 Temporal Cytokine Response:

MC38 tumors were treated intratumorally with scIL-12 in PLE terminal Ni conjugated particles after tumors were allowed to establish for 7 days. Tumors were extracted at different time points, homogenized, and analyzed via ELISA for a cytokine response. The resulting data are presented in FIG. 7. These data show that scIL-12 in Ni-HIS particles with PLE terminal layer are able to incite an immune response in the tumor lasting approximately 5-7 days.

Figure 8A:
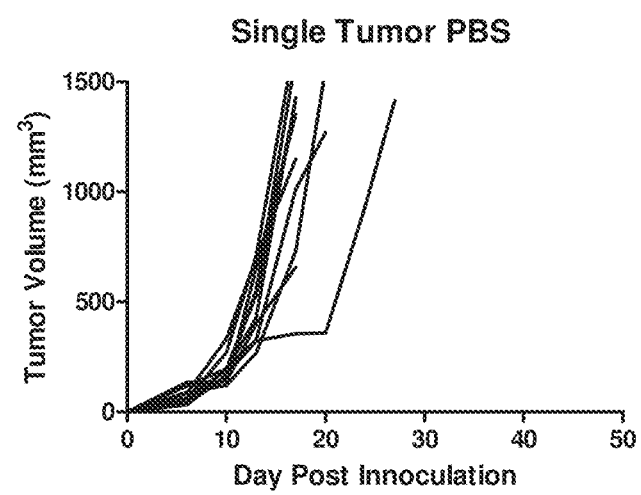
FIGS. 8A-8H show efficacy of the PLE terminal Ni conjugated scIL-12 nanoparticles treatment on the MC38 mice tumors. The data show individual mice tumor volumes by treatment, comparison of average tumor volumes on Day 13, and survival across treatment groups.
Figure 8B:
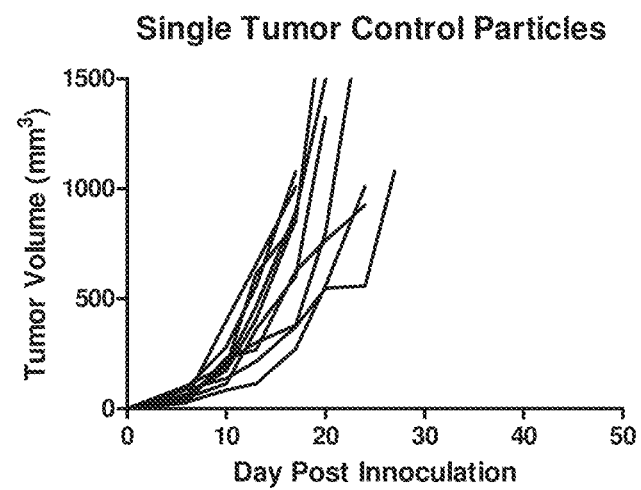
Figure 8C:
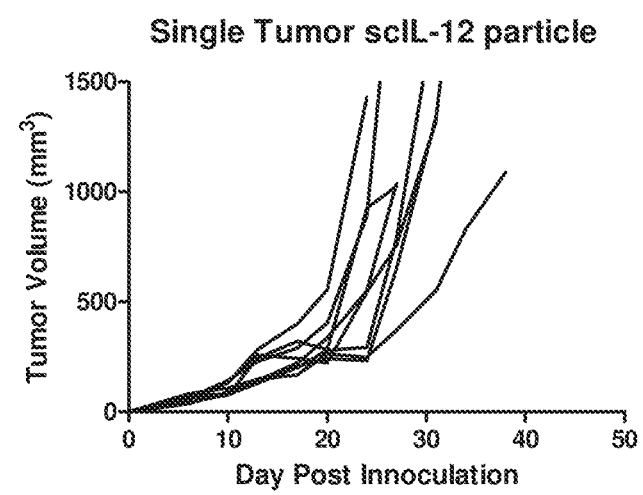
Figure 8D:
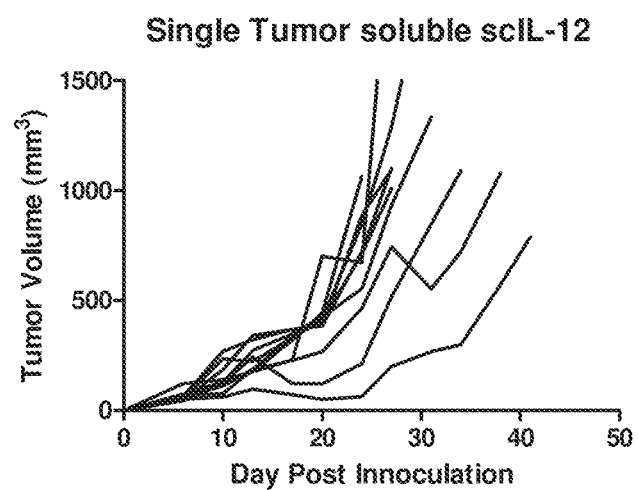
Figure 8E:
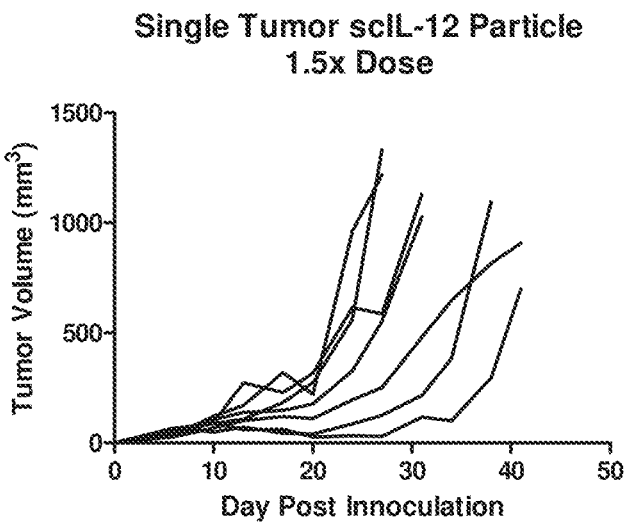
Figure 8F:
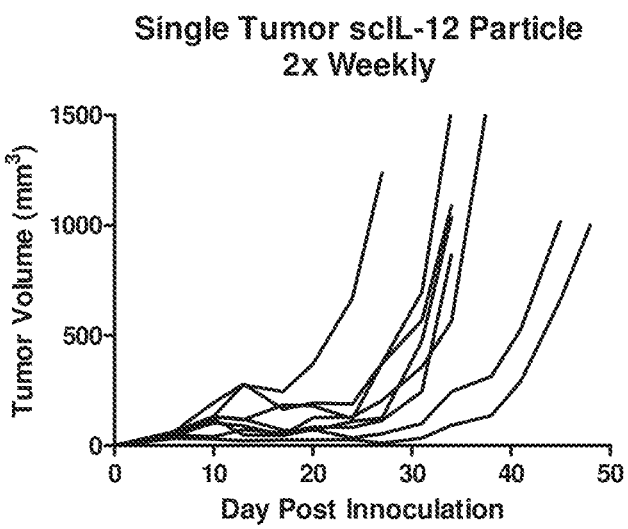
Figure 8G:
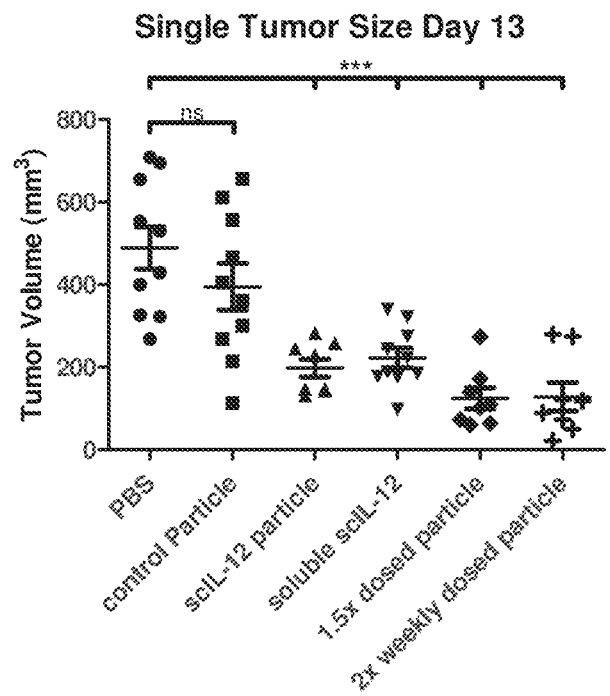
Figure 8H:
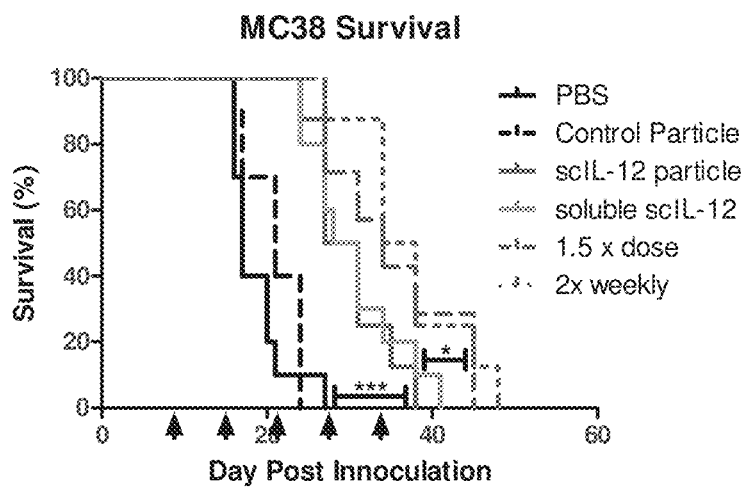

MC38 In Vivo Efficacy:

MC38 tumors were established on the right flank of C57Bl/6 mice and allowed to grow for 6 days. On day 6 treatments were begun intratumorally. Mice were treated weekly with PBS, weekly with control particles (no IL-12), weekly with PLE terminal Ni conjugated scIL-12 at 5 μg dose, weekly with 5 μg soluble scIL-12, weekly with 7.5 μg scIL-12 in particles, or twice weekly with 5 μg scIL-12 in particles. All treatments were given for 5 doses. Data presented in FIGS. 8A-8F show individual mice tumor volumes by treatment, FIG. 8G shows comparison of average tumor volumes on Day 13, and FIG. 8H shows survival across treatment groups. Particle bound scIL-12 performs as well as soluble with the potential for improvement at increased frequency or amount of dosing.

Figure 9A:
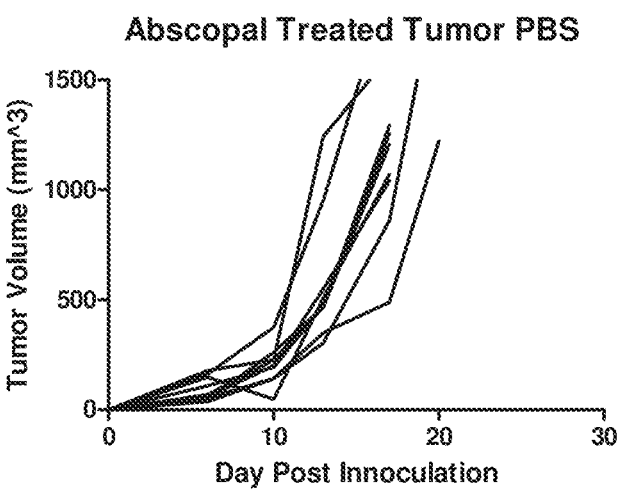
FIGS. 9A-9I show MC38 tumors abscopal response to the treatment with PLE terminal Ni conjugated scIL-12 nanoparticles. Data show tumor volume of both treated and contralateral tumors, average tumor sizes on day 17, and survival.
Figure 9B:
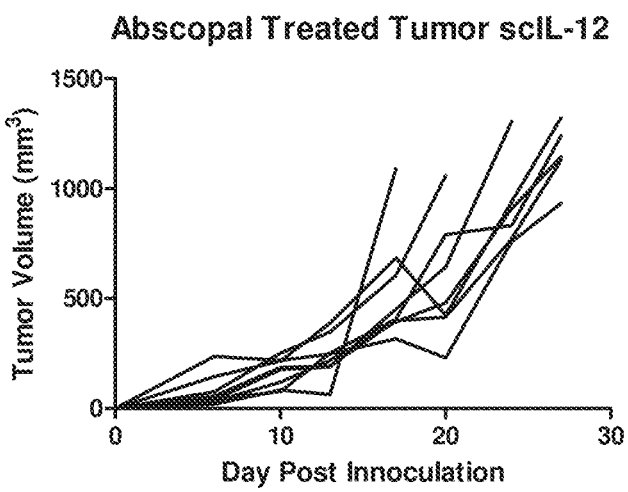
Figure 9C:
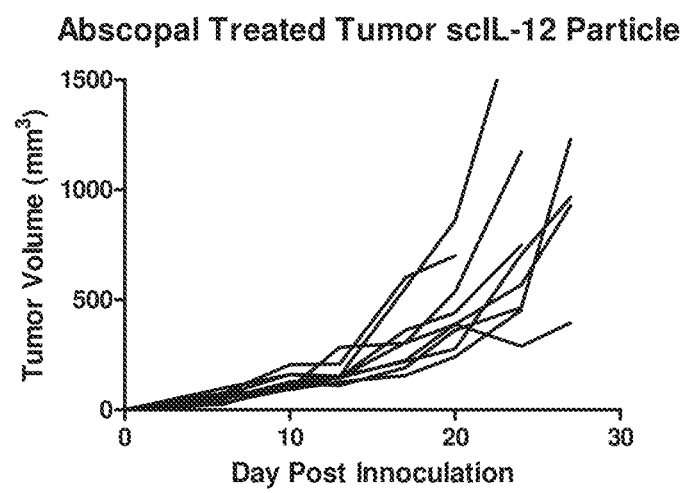
Figure 9D:
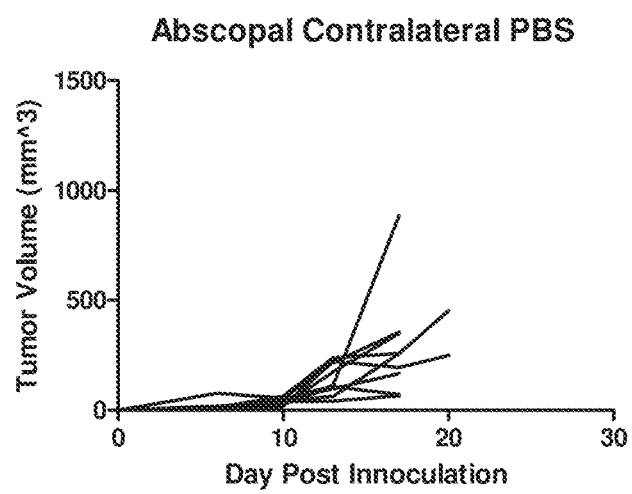
Figure 9E:
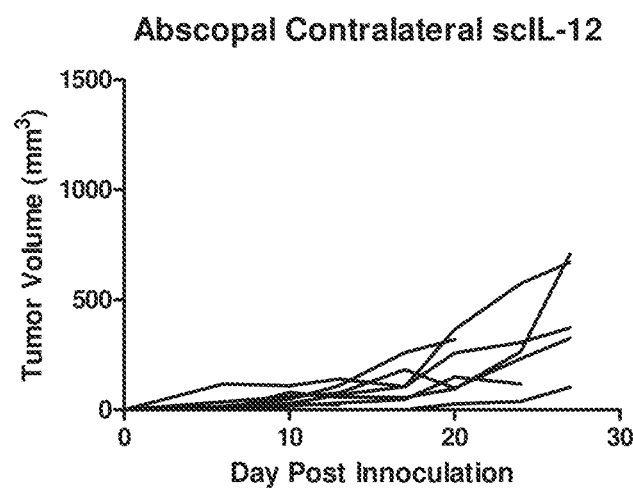
Figure 9F:
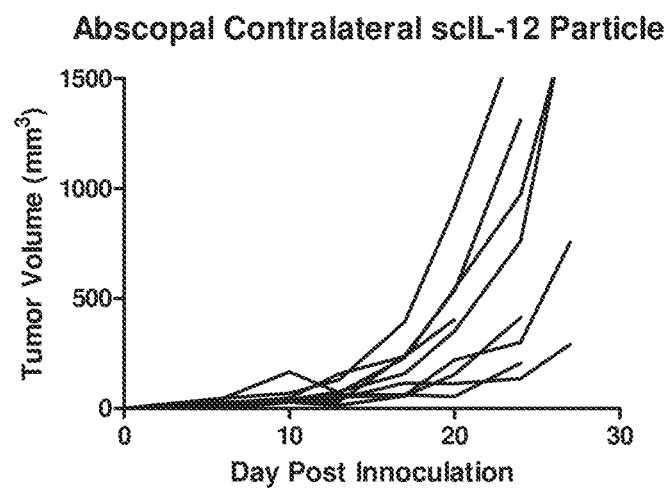
Figure 9G:
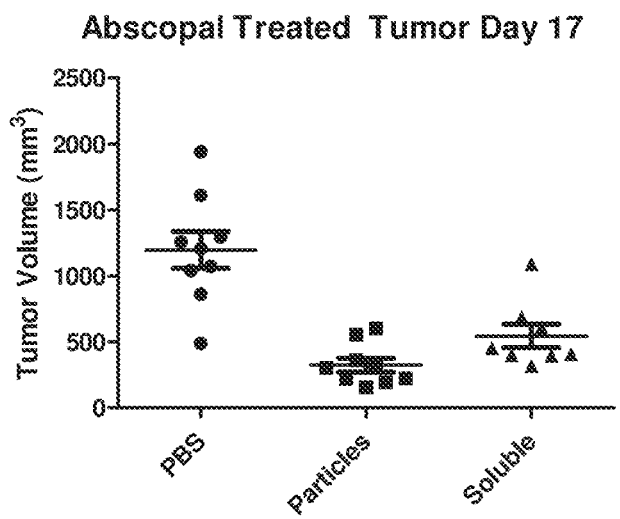
Figure 9H:
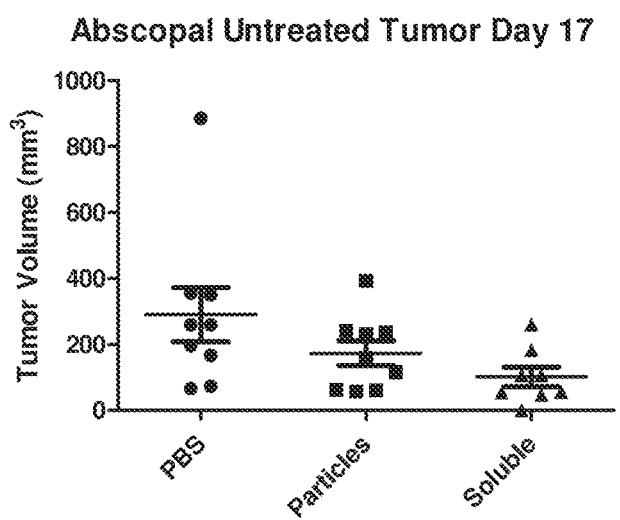
Figure 9I:
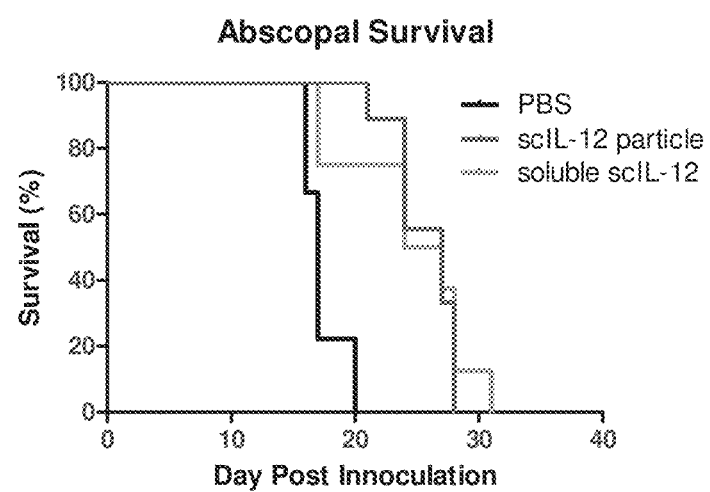

MC38 Abscopal Response:

Tumors were established on both left and right flank of C57Bl/6 mice. Right flank tumors were treated day 6 after inoculation with PBS, 5 µg scIL-12 in particles or 5 µg scIL-12 soluble on a weekly basis for 5 doses. Data presented in FIGS. 9A-9F show tumor volume of both treated and contralateral tumors, FIGS. 9G-9H shows average tumor sizes on day 17, and FIG. 9I shows survival. Particles perform similar to soluble cytokine in the treated tumor, but slightly worse in contralateral tumors likely due to systemic leakage of the free cytokine, as exemplified in the toxicity data.

Figure 10A:
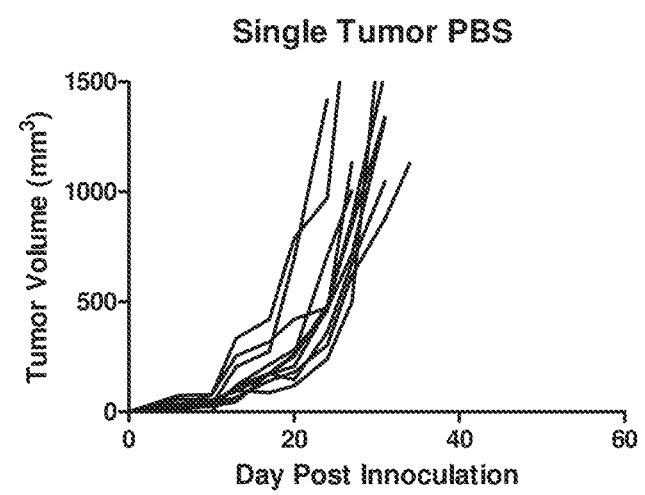
FIGS. 10A-10F shows efficacy of the PLE terminal Ni conjugated scIL-12 nanoparticles treatment on the HM-1 mice tumors. Data show individual mice tumor volumes by treatment, comparison of average tumor volumes on Day 27, and survival across treatment groups.
Figure 10B:
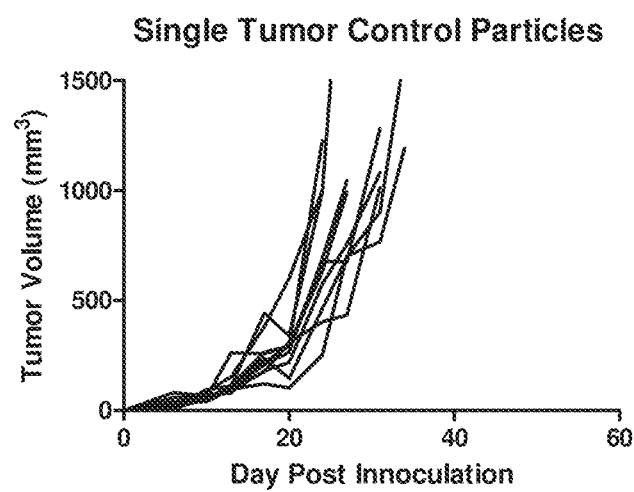
Figure 10C:
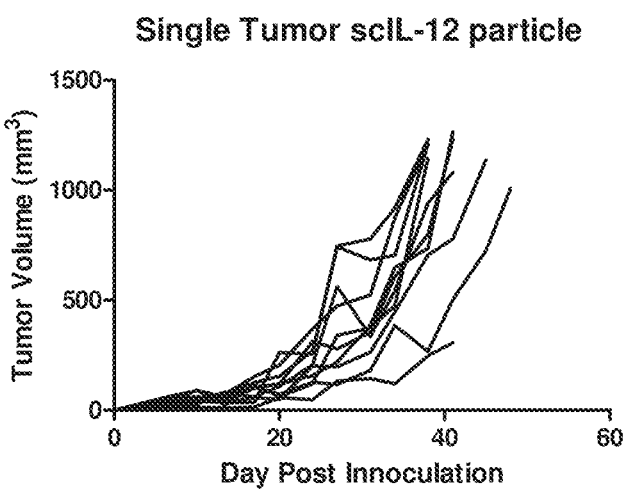
Figure 10D:
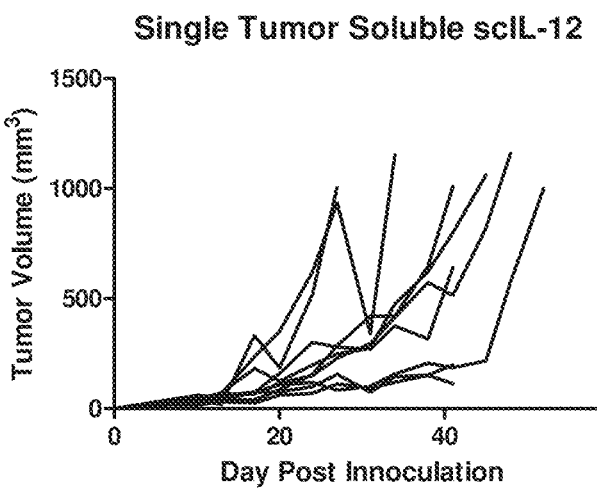
Figure 10E:
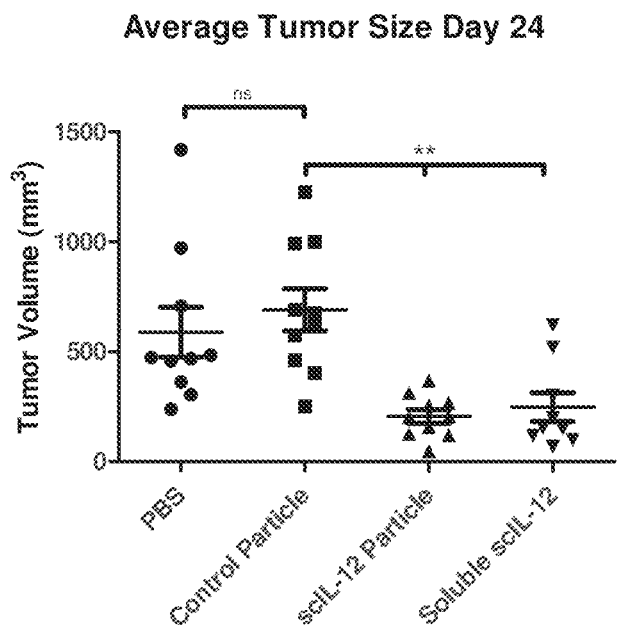
Figure 10F:
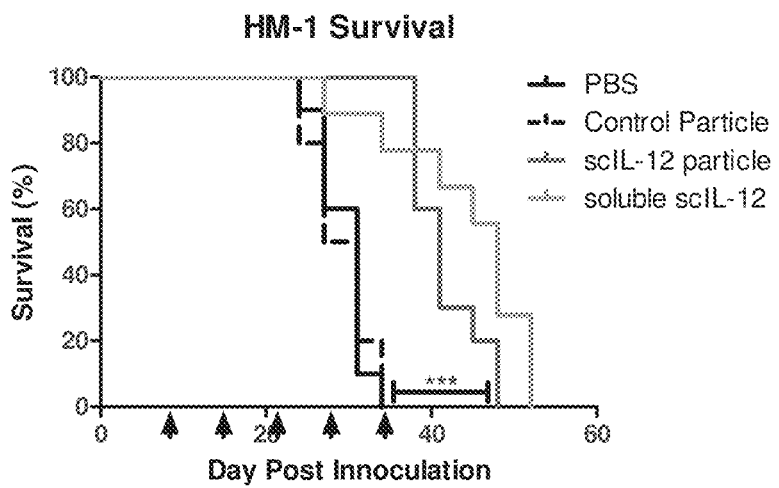

HM-1 In Vivo Efficacy:

HM-1 tumors were established on the right flank of B6C3F1 mice (pairings of C57BL/6× C3H/HeN) and allowed to grow for 6 days. On day 6 treatments were begun intratumorally. Mice were treated weekly with PBS, weekly with control particles (no IL-12), weekly with PLE terminal Ni conjugated scIL-12 at 5 µg dose, weekly with 5 µg soluble scIL-12. Data presented in FIGS. 10A-10D show individual mice tumor volumes by treatment, FIG. 10E shows comparison of average tumor volumes on Day 24, and FIG. 10F shows survival across treatment groups. Particle bound scIL-12 performs as well as soluble with the potential for improvement at increased frequency or amount of dosing.

Particle immune activity will be tested by testing efficacy of treatment on contralateral tumors and rechallenging subjects that respond to treatment with additional tumor cells.

Example 5—Treatment Scheduling

Various treatment schedules will be examined. Specific tumor targeting and biodistribution will be tested as a function of dosing schedule.

Example 6—Combination Therapies

Combination therapy particles will be formulated by including additional drugs (chemotherapy, synergistic cytokines, etc.) in unused particle compartments (liposome core, layers).

INCORPORATION BY REFERENCE

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicant reserves the right to physically incorporate into this application any and all materials and information from any such articles, patents, patent applications, or other physical and electronic documents.

EQUIVALENTS

The inventions have been described broadly and generically herein. Those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The inventions are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of embodiments of the invention. Further, each of the narrower species and subgeneric groupings falling within the generic disclosure also form parts of the inventions. This includes the generic description of embodiments of the invention with a proviso or negative limitation removing any subject matter from the genus, regardless of whether or not the excised material is specifically recited herein.

We claim:

1. A particle comprising:
    a liposome, wherein the liposome comprises a first lipid covalently bonded to an affinity ligand; and the first lipid forms an outer surface of the liposome;
    a cytokine covalently bonded to a tag, wherein the tag is associated with the affinity ligand, and wherein the cytokine binds a receptor on the surface of an immune cell when the particle contacts a cancer cell; and
    a polymer coating, wherein the polymer coating comprises:
    at least one layer including a polycation, wherein the polycation is non-covalently associated with the outer surface of the liposome; and
    at least one layer including polyglutamic acid, wherein the polyglutamic acid is non-covalently associated with the at least one polycation layer.

2. The particle of claim 1, further comprising a metal ion, wherein:
    the affinity ligand is a metal-affinity ligand;
    the tag is a peptide tag;
    the metal ion is coordinated with the metal-affinity ligand, thereby forming a metal-coordinated ligand;
    the peptide tag is associated with the metal-coordinated ligand.

3. The particle of claim 2, wherein the metal-coordinated ligand is non-covalently associated with the peptide tag.

4. The particle of claim 3, wherein the metal-affinity ligand is iminodiacetic acid or iminodipropionic acid.

5. The particle of claim 3, wherein the metal ion is selected from the group consisting of Fe(III), Co(II), Ni(II), Cu(II), and Zn(II).

6. The particle of claim 3, wherein the peptide tag is at least two amino acid monomers in length.

7. The particle of claim 3, wherein the peptide tag comprises a histidine monomer.

8. The particle of claim 1, wherein the first lipid is 1,2-dioleoyl-sn-glycero-3-[(N-(5-amino-1-carboxypentyl) iminodiacetic acid)succinyl].

9. The particle of claim 1, wherein the liposome further comprises a second lipid; and the second lipid is a phosphatidylcholine.

10. The particle of claim 1, wherein the liposome further comprises a third lipid.

11. The particle of claim 1, wherein the liposome further comprises a fourth lipid; and the fourth lipid is cholesterol.

12. The particle of claim 1, wherein the tag is non-covalently associated with the affinity ligand on the outer surface of the liposome.

13. The particle of claim 1, wherein the tag is covalently associated with the affinity ligand on the outer surface of the liposome.

14. The particle of claim 1, wherein the cytokine is a single-chain variant of IL-12.

15. The particle of claim 1, wherein the polycation is selected from the group consisting of polyarginine and polylysine.

16. The particle of claim 1, wherein the particle further comprises a second polycation coating non-covalently associated with the outer surface of the polyglutamic acid coating; and a second polyglutamic acid coating non-covalently associated with the outer surface of the second polycation coating.

17. The particle of claim 1, wherein
the first lipid covalently bonded to the affinity ligand is 1,2-dioleoyl-sn-glycero-3-[(N-(5-amino-1-carboxypentyl)iminodiacetic acid)succinyl];
the particle further comprises a metal ion selected from the group consisting of Fe(III), Co(II), Ni(II), Cu(II), and Zn(II);
the metal ion is coordinated with the affinity ligand, thereby forming a metal-coordinated ligand;
the metal-coordinated ligand is non-covalently associated with the tag;
the tag is a peptide tag;
the peptide tag is at least two amino acid monomers in length;
the peptide tag comprises a histidine monomer;
the cytokine is a single-chain variant of IL-12; and
the polycation is selected from the group consisting of polyarginine and polylysine.

18. The particle of claim 1, wherein the at least one layer including polyglutamic acid has an affinity for the cancer cell.

19. A pharmaceutical formulation comprising a plurality of particles of claim 1, and a pharmaceutically acceptable carrier.

20. A method of treating cancer comprising administering to a subject in need thereof a therapeutically effective amount of a particle of claim 1.

21. The method of claim 20, wherein the cancer is colon cancer or ovarian cancer.

* * * * *